(12) United States Patent
Shin et al.

(10) Patent No.: US 11,286,296 B2
(45) Date of Patent: Mar. 29, 2022

(54) ANTI-HUMAN NINJURIN-1 (NINJ-1) ANTIBODIES AND METHODS FOR DETECTING HUMAN NINJ-1

(71) Applicants: ABION INC., Seoul (KR); SEOUL NATIONAL UNIVERSITY R&DB FOUNDATION, Seoul (KR)

(72) Inventors: Young Kee Shin, Seoul (KR); Seahyung Lee, Seongnam-si (KR); Kyoung Song, Seoul (KR); Ji Hye Lee, Hwaseong-si (KR)

(73) Assignees: ABION INC., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 255 days.

(21) Appl. No.: 16/328,522

(22) PCT Filed: Aug. 28, 2017

(86) PCT No.: PCT/KR2017/009377
§ 371 (c)(1),
(2) Date: May 2, 2019

(87) PCT Pub. No.: WO2018/038583
PCT Pub. Date: Mar. 1, 2018

(65) Prior Publication Data
US 2019/0248878 A1 Aug. 15, 2019

(30) Foreign Application Priority Data
Aug. 26, 2016 (KR) .................. 10-2016-0109557

(51) Int. Cl.
| | |
|---|---|
| A61K 39/395 | (2006.01) |
| A61K 39/00 | (2006.01) |
| A61K 49/00 | (2006.01) |
| A61K 49/16 | (2006.01) |
| C07K 16/00 | (2006.01) |
| C07K 16/18 | (2006.01) |
| G01N 33/53 | (2006.01) |
| G01N 33/68 | (2006.01) |
| A61P 25/28 | (2006.01) |
| A61P 35/04 | (2006.01) |

(52) U.S. Cl.
CPC .......... *C07K 16/18* (2013.01); *A61P 25/28* (2018.01); *A61P 35/04* (2018.01); *G01N 33/68* (2013.01); *C07K 2317/34* (2013.01); *C07K 2317/515* (2013.01); *C07K 2317/565* (2013.01)

(58) Field of Classification Search
CPC .......... A61K 2039/505; A61K 39/3955; A61K 39/00; A61K 38/1709; C07K 2317/92; C07K 16/18; C07K 16/28; C07K 16/2803; C07K 2317/515; C07K 2317/565; C07K 2317/622; C07K 14/475; C07K 14/4702; C07K 14/71; A61P 25/28; A61P 25/00; A61P 35/00
See application file for complete search history.

(56) References Cited

U.S. PATENT DOCUMENTS

| | | | | |
|---|---|---|---|---|
| 8,618,072 B2 * | 12/2013 | Kim | ........................ | A61P 25/00 514/44 A |
| 8,703,711 B2 * | 4/2014 | Prat | ........................ | A61P 25/00 514/17.9 |
| 9,138,474 B2 * | 9/2015 | Kim | .................... | A61K 39/3955 |
| 2010/0310568 A1 * | 12/2010 | Prat | ...................... | C12Q 1/6883 424/139.1 |
| 2011/0123538 A1 * | 5/2011 | Kim | ........................ | A61P 17/00 424/139.1 |
| 2014/0037640 A1 * | 2/2014 | Kim | ...................... | A61K 31/00 424/139.1 |

FOREIGN PATENT DOCUMENTS

| | | | |
|---|---|---|---|
| WO | WO2014/095916 | * | 6/2014 |
| WO | WO 2014/095916 | | 6/2014 |
| WO | WO 2015/023054 | | 2/2015 |

OTHER PUBLICATIONS

MacCallum et al., J. Mol. Biol., 1996; 262: 732-745.*
Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al., J of Cell Bio. 1990, 111:2129-2138.*
Bowie et al. Science, 1990, 247:1306-1310.*
Pawson et al. 2003, Science 300:445-452.*

(Continued)

*Primary Examiner* — Chang-Yu Wang
(74) *Attorney, Agent, or Firm* — James S. Keddie; Bozicevic, Field & Francis LLP

(57) ABSTRACT

The present invention provides: an antibody which specifically bonds to human NINJ-1; and a fragment thereof. The antibody or the fragment thereof according to the present invention has very high bonding affinity and bonding specificity with respect to a human NINJ-1 or a homogeneous binding site of the protein, and does not exhibit cross-reactivity with NINJ-1 proteins that are derived from other organisms and have high protein similarity. Accordingly, the present invention provides significant advantages with respect to accuracy and sensitivity and the like, not only in diagnosing disease related to NINJ-1 proteins but also in inhibiting pathological conditions involving NINJ-1 proteins. In particular, the antibody provided according to the present invention has a remarkable effect of inhibiting attachment between immunocytes and human cerebral endothelial cells, and thus has an effect of treating multiple sclerosis.

8 Claims, 15 Drawing Sheets

Specification includes a Sequence Listing.

(56) References Cited

OTHER PUBLICATIONS

Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
Anti-human Nijurin-1 antibody catalog No. MAB51051 retreived from the R& D systems website: resources.rndsystems.com/pdfs/datasheets/mab51051.pdf?v=20210308 on Mar. 8, 2021.*
Anti-human Nijurin-1 antibody (MA5-24365) from the thermofisher website: www.thermofisher.com/order/genome-database/dataSheetPdf?producttype=antibody&productsubtype=antibody_primary&productId=MA5-24365&version=133, retreived on Mar. 8, 2021.*
Ifergan et al., Ann. Neurol. 2011; 70:751-763.*
Ahn et al., "Ninjurin1 Deficiency Attenuates Susceptibility of Experimental Autoimmune Encephalomyelitis in Mice", The Journal of Biological Chemistry, 2014, 289(6): 3328-3338.
Ortiz et al., "Role of the Blood-Brain Barrier in Multiple Sclerosis", Archives of Medical Research, 2014, 11 pages.
Kanda, "Molecular targeted therapy against the blood-brain barrier in multiple sclerosis", Clinical and Experimental Neuroimmunology, 2014, 5 (Suppl. 1), 28-34.

\* cited by examiner

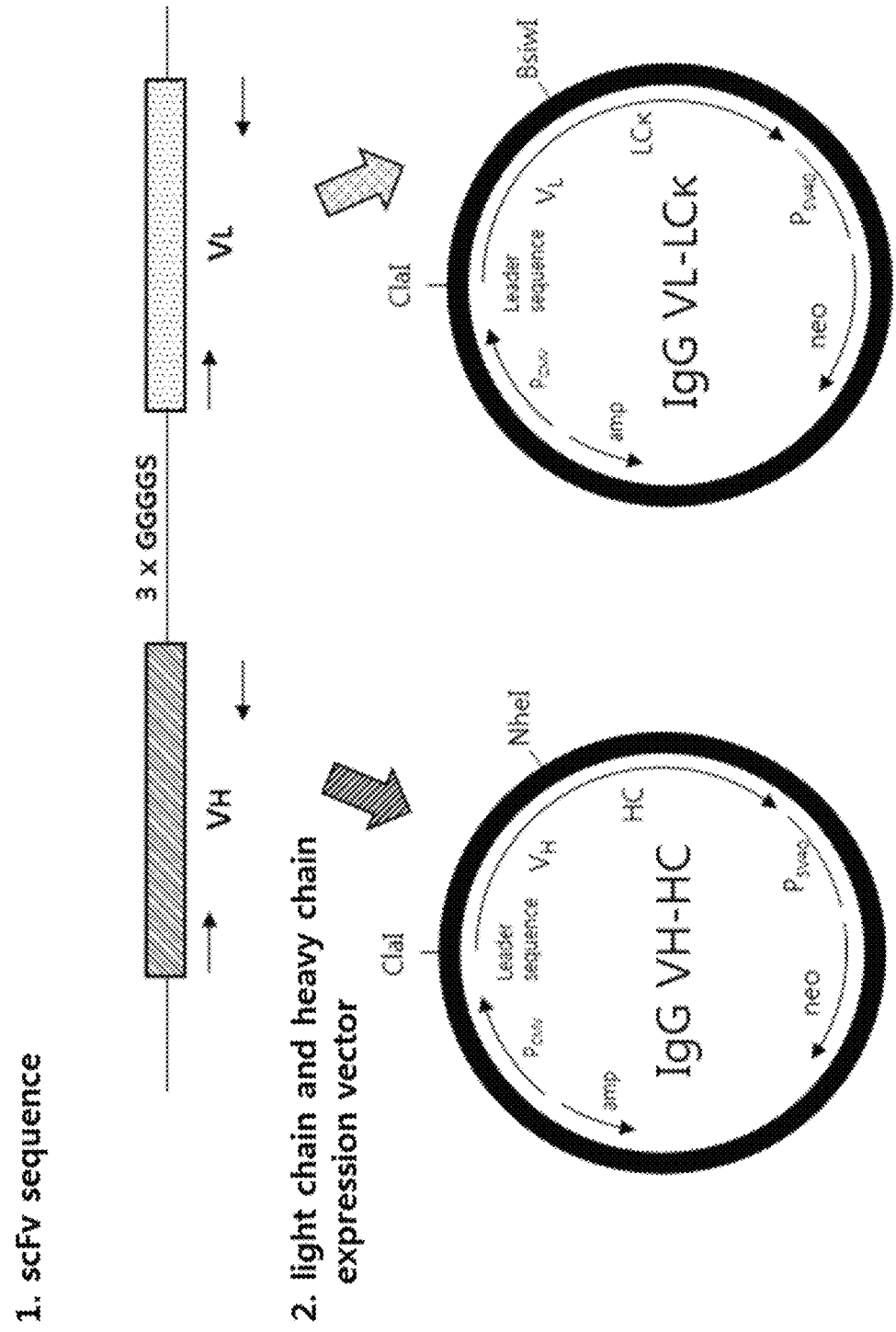

ANTI-HUMAN NINJURIN-1 (NINJ-1) ANTIBODIES AND METHODS FOR DETECTING HUMAN NINJ-1

CROSS-REFERENCE TO RELATED APPLICATIONS

This application is a § 371 national phase of International Application No. PCT/KR2017/009377, filed on Aug. 28, 2017, which claims the benefit of Korean Application No. 10-2016-0109557, filed on Aug. 26, 2016, which applications are incorporated by reference herein.

TECHNICAL FIELD

The present invention relates to an anti-NINJ-1 (Ninjurin-1) antibody and use of the same. More particularly, the present invention relates to an antibody or antigen-binding fragment thereof that binds to human NINJ-1, a method for preparing the same, and a composition comprising the same for preventing or treating multiple sclerosis or cancer.

BACKGROUND OF THE INVENTION

The present application claims priority from Korean Patent Application No. 10-2016-0109557, filed on Aug. 26, 2016, the entire content of which is incorporated herein by reference.

Ninjurin-1 (NINJ-1) was first reported in 1996 by Toshiyuki Araki et al (Araki, T. & Milbrandt, J., Neuron 17, 353-361, 1996). It had been found in the process of finding a gene whose expression increases in Schwann cells after damages caused by transection or crushing of the distal part of the sciatic nerve.

A phylogenetic tree has been reported to find proteins with homology to Ninjurin using protein information known from GenBank. In vertebrates, two Ninjurin proteins, such as Ninjurin1 (NINJ1) and Ninjurin-2 (NINJ-2), are known, respectively. The NINJ-1 and NINJ-2 have been found in vertebrates such as humans, mice and rats. In invertebrates, Ninjurin proteins can be divided into three types, such as A type, B type, and C type, while being found in *Drosophila* and Mosquitoes, and the like. Human NINJ-1 and mouse NINJ-1 proteins are 90% identical each other, while human NINJ-1 and human NINJ-2 are 55% identical.

Human NINJ-1 is located in the chromosome 9q22 and composed of 152 amino acids. Mouse NINJ-1 is located in the chromosome 13 and composed of 152 amino acids. In the amino acid sequence of NINJ-1, it is suspected that there may be two transmembrane domains. It is also known that NINJ-1 is a protein located in the cell membrane through experiments (Araki, T. & Milbrandt, J., Neuron 17, 353-361, 1996). This fact suggests that the N-terminal region of NINJ-1 may extend out of the cell. NINJ-1 is known to bind homologous proteins through experiments, while it is known that the NINJ-1 expression rate increases in an inflammatory environment or an animal model of multiple sclerosis and is mainly involved in the motility and transendothelial migration of cancer and immune cells. In particular, a residue region between P26 and N37 in the extracellular portion of NINJ-1 is known to be a crucial domain for homologous binding, while disease mitigation has been reported when administering a neutralizing antibody or a fragment-binding peptide for that position (Ifergan I et al., Ann Neurol. 70(5):751-763, 2011; Ahn B J et al., J Biol Chem. 289(6): 3328-3338, 2014; Odoardi F. et al., Nature. 488(7413):675-679, 2012).

NINJ-1 is expressed in various tissues. For example, it has been reported that in the RNA level, it is expressed in the heart, brain, placenta, lung, liver, skeletal muscles, kidney, pancreas, spleen, thymus, prostate, testis, ovary, small intestine, colon, blood, adrenal gland and Dorsal Root Ganglia (DRG), while in the protein phase, it is expressed in the liver, kidney, thymus, uterus, adrenal gland, retina and DRG, respectively.

In addition, the functions of NINJ-1 so far known are related to cell adhesion, neurite outgrowth, cellular senescence and cancer (See Proceedings of the National Academy of Sciences of the United States of America. 110(23), pp. 9362-9367(2013 Jun. 4.)).

However, despite the importance of human NINJ-1 as a biomarker, there is no technology capable of detecting human NINJ-1 with high sensitivity and accuracy. In particular, the human NINJ-1 protein has similarities to that of mouse NINJ-1 in many aspects of a protein structure, and thus antibodies obtained by conventional methods known in the art by immunological reaction from animals have problems such as a cross-reaction in which binding to mouse NINJ-1 occurs, and highly sensitive antibodies against human NINJ-1 have been failed to be produced in many cases.

DETAILED DESCRIPTION OF THE INVENTION

Technical Problem

Accordingly, the present inventors have conducted studies to develop an antibody that specifically binds to human NINJ-1 protein or homologous binding site of the protein. During the study, it was confirmed that the antibody and the antigen-binding fragment thereof having the unique CDR sequence structure disclosed herein specifically bind to the human NINJ-1 protein without cross-reactivity with other NINJ-1 protein (especially, mouse NINJ-1 protein), thereby completing the present invention.

Accordingly, an aspect of the present invention is to provide an antibody or antigen-binding fragment thereof that specifically binds to a human-derived Ninjurin-1 (NINJ-1) protein.

Another aspect of the present invention is to provide a polynucleotide encoding the antibody or antigen-binding fragment thereof.

Another aspect of the present invention is to provide a vector comprising the polynucleotide.

Another aspect of the present invention is to provide a cell comprising the vector.

Another aspect of the present invention is to provide a method for preparing an antibody or a antigen-binding fragment thereof that specifically binds to a human NINJ-1 protein using the cell.

Another aspect of the present invention is to provide a method of specifically detecting human NINJ-1, the method comprising the steps of:

contacting the antibody or a antigen-binding fragment thereof specifically binding to the human-derived NINJ-1 protein of the present invention with a sample; and detecting the antibody or antigen-binding fragment thereof.

Another aspect of the present invention is to provide a pharmaceutical composition for preventing or treating multiple sclerosis, the composition comprising the antibody or antigen-binding fragment thereof specifically binding to the human-derived NINJ-1 protein of the present invention as an active ingredient.

Another aspect of the present invention is to provide a pharmaceutical composition for preventing or treating cancer and for inhibiting cancer metastasis, the composition comprising the antibody or antigen-binding fragment thereof specifically binding to the human-derived NINJ-1 protein of the present invention as an active ingredient.

Technical Solution

An embodiment according to an aspect of the present invention provides an antibody or antigen-binding fragment thereof that specifically binds to a human-derived Ninjurin-1 (NINJ-1) protein.

An embodiment according to another aspect of the present invention provides a polynucleotide encoding the antibody or antigen-binding fragment thereof.

An embodiment according to another aspect of the present invention provides a vector comprising the polynucleotide.

An embodiment according to another aspect of the present invention provides a cell comprising the vector.

An embodiment according to another aspect of the present invention provides a method for preparing an antibody or a antigen-binding fragment thereof that specifically binds to a human NINJ-1 protein, the method comprising the steps of: culturing the cell under the condition that a polynucleotide is expressed, thereby producing a polypeptide comprising a light chain variable region and a heavy chain variable region; and recovering a polypeptide from the cell or a medium in which the cell has been cultured.

An embodiment according to another aspect of the present invention provides a method of specifically detecting human NINJ-1, the method comprising the steps of: contacting the antibody or antigen-binding fragment thereof specifically binding to the human-derived NINJ-1 protein with a sample; and detecting the antibody or fragment thereof.

An embodiment according to another aspect of the present invention provides a pharmaceutical composition for preventing or treating multiple sclerosis, the composition comprising the antibody or antigen-binding fragment thereof specifically binding to the human-derived NINJ-1 protein of the present invention as an active ingredient.

An embodiment according to another aspect of the present invention provides a pharmaceutical composition for preventing or treating cancer and for inhibiting cancer metastasis, the composition comprising the antibody or antigen-binding fragment thereof specifically binding to the human-derived NINJ-1 protein of the present invention as an active ingredient.

Hereinafter, the present invention will be described in detail.

The present invention provides an antibody or antigen-binding fragment thereof that specifically binds to a human-derived Ninjurin-1 (NINJ-1) protein.

As used herein, the term 'antibody' is also referred to as immunoglobulin (Ig), and is a generic term of proteins involved in biologic immunity by selectively acting on antigens. Whole antibodies found in nature are generally composed of two pairs of light chain (LC) and heavy chain (HC), which are polypeptides consisting of several domains, or two pairs of these HC/LC structures as a base unit. There are five types of heavy chains that make up mammalian antibodies: the Greek letters α, δ, ε, γ, and μ. Depending on the type of heavy chain, IgA, IgD, IgE, IgG and IgM, respectively, constitute different types of antibodies. There are two types of light chains that constitute mammalian antibodies, represented by Δ and κ.

The heavy chains and light chains of the antibody are structurally divided into variable regions and constant regions according to the variability of the amino acid sequence. The constant region of the heavy chain composed of 3 or 4 heavy chain constant regions such as CH1, CH2 and CH3 (IgA, IgD and IgG antibodies) and CH4 (IgE and IgM antibodies), depending on the type of antibody, while the light chain is composed of one constant region CL. The variable region of the heavy chain and the light chain composed of one domain of the heavy chain variable region (VH) and the light chain variable region (VL), respectively. The light chains and heavy chains are linked by one covalent disulfide bond, with each variable region and constant region aligned side by side, and the heavy chain of the two molecules bound to the light chain is linked through two covalent disulfide bonds to form an entire antibody. The whole antibody binds specifically to an antigen through the variable regions of the heavy chains and light chains. The whole antibody is composed of two heavy chain and light chain pairs (HC/LC), so that one molecule of the whole antibody has a single specificity of bivalent binding to two identical antigens through two variable regions.

The variable region comprising a site where the antibody binds to the antigen is subdivided into a framework region (FR) with low sequence variability and a complementarity determining region (CDR) which is a hypervariable region with high sequence variability. CDR-L1 is positioned appropriately at residues 24-34, CDR-L2 appropriately at residues 50-56, and CDR-L3 appropriately at residues 89-97 in the light chain variable region; and CDR-H1 is positioned appropriately at residues 31-35, CDR-H2 appropriately at residues 50-65, and CDR-H3 appropriately at residues 95-102 in the heavy chain variable region. VH and VL of three CDRs and four FRs are arranged in the order of FR1-CDR1-FR2-CDR2-FR3-CDR3-FR4 in the direction of N-terminus to C-terminus, respectively. This is a site where the CDR with the highest sequence variability within the variable region of the antibody binds directly to the antigen, while being the most important site for the antigen specificity of the antibody.

The term 'Ninjurin-1 (NINJ-1)' is a type of cell membrane protein and human NINJ-1 as used herein, is meant to include both native and recombinant human NINJ-1. The protein sequence of the wild-type human NINJ-1 is known in the art as NCBI (genbank) Reference Sequence: NP_004139.2 (SEQ ID NO: 25). As a polynucleotide sequence encoding the above protein, NCBI (genbank) Reference Sequence: NM_004148.3 (SEQ ID NO: 26) is known, and a person skilled in the art can obtain a recombinant protein accordingly.

The present inventors have developed the antibody and antigen-binding fragment thereof which specifically bind to the 26th to the 37th amino acid residues in the human-derived NINJ-1 protein sequence defined by SEQ ID NO: 25. Through the unique variable region CDR sequence structure of these antibodies, it was confirmed that the effect of their specific binding to human NINJ-1 protein was remarkable without showing any cross-reactivity with other origin-derived NINJ-1 proteins (especially, mouse NINJ-1 protein).

Specifically, the antibody or antigen-binding fragment thereof of the present invention comprises a light chain variable region (VL) and a heavy chain variable region (VH) comprising specific CDR sequences as follows:

the antibody or antigen-binding fragment thereof comprises an antibody light chain variable region (VL) comprising a complementarity determining region (CDR) L1 comprising the amino acid sequence defined by SEQ ID NO: 1, a complementarity determining region (CDR) L2 comprising the amino acid sequence defined by SEQ ID NO: 2, and a complementarity determining region (CDR) L3 comprising the amino acid sequence defined by SEQ ID NO: 3; and an antibody heavy chain variable region (VH) comprising a complementarity determining region (CDR) H1 comprising the amino acid sequence defined by SEQ ID NO: 4, a complementary determining region (CDR) H2 comprising the amino acid sequence defined by SEQ ID NO: 5, and a complementarity determining region (CDR) H3 comprising the amino acid sequence defined by SEQ ID NO: 6, the antibody or antigen-binding fragment thereof comprises an antibody light chain variable region (VL) comprising a complementarity determining region (CDR) L1 comprising the amino acid sequence defined by SEQ ID NO: 7, a complementarity determining region (CDR) L2 comprising the amino acid sequence defined by SEQ ID NO: 8, and a complementarity determining region (CDR) L3 comprising the amino acid sequence defined by SEQ ID NO: 9; and an antibody heavy chain variable region (VH) comprising a complementarity determining region (CDR) H1 comprising the amino acid sequence defined by SEQ ID NO: 10, a complementary determining region (CDR) H2 comprising the amino acid sequence defined by SEQ ID NO: 11, and a complementarity determining region (CDR) H3 comprising the amino acid sequence defined by SEQ ID NO: 12, the antibody or antigen-binding fragment thereof comprises an antibody light chain variable region (VL) comprising a complementarity determining region (CDR) L1 comprising the amino acid sequence defined by SEQ ID NO: 13, a complementarity determining region (CDR) L2 comprising the amino acid sequence defined by SEQ ID NO: 14, and a complementarity determining region (CDR) L3 comprising the amino acid sequence defined by SEQ ID NO: 15; and an antibody heavy chain variable region (VH) comprising a complementarity determining region (CDR) H1 comprising the amino acid sequence defined by SEQ ID NO: 16, a complementary determining region (CDR) H2 comprising the amino acid sequence defined by SEQ ID NO: 17, and a complementarity determining region (CDR) H3 comprising the amino acid sequence defined by SEQ ID NO: 18, the antibody or antigen-binding fragment thereof comprises an antibody light chain variable region (VL) comprising a complementarity determining region (CDR) L1 comprising the amino acid sequence defined by SEQ ID NO: 19, a complementarity determining region (CDR) L2 comprising the amino acid sequence defined by SEQ ID NO: 20, and a complementarity determining region (CDR) L3 comprising the amino acid sequence defined by SEQ ID NO: 21; and an antibody heavy chain variable region (VH) comprising a complementarity determining region (CDR) H1 comprising the amino acid sequence defined by SEQ ID NO: 22, a complementary determining region (CDR) H2 comprising the amino acid sequence defined by SEQ ID NO: 23, and a complementarity determining region (CDR) H3 comprising the amino acid sequence defined by SEQ ID NO: 24.

The antibody specifically binding to the human NINJ-1 protein according to the present invention is not limited as long as it has the above-described combination of CDRs. Specifically, it may be selected from the group consisting of IgG, IgA, IgM, IgE, and IgD, and is preferably an IgG antibody.

In addition, it may be a monoclonal antibody derived from one B cell or a polyclonal antibody derived from a plurality of B cells, but is preferably a monoclonal antibody which is a group of antibodies having substantially the same amino acid sequence in the heavy chain and light chain of the antibody. As used herein, the term "monoclonal" refers to such characteristics of an antibody as antibodies obtained from a substantially homogenous population, and is not construed as requiring the production of an antibody by a particular method. For example, the monoclonal antibodies as used herein may be prepared by the hybridoma method first described by Kohler et al. (1975) Nature 256:495), or may be prepared by a recombinant DNA method (see, U.S. Pat. No. 4,816,567). The monoclonal antibodies may also be isolated from phage antibody libraries using the techniques described in, for example, Clackson et al. (1991) Nature 352:624-628; Marks et al. (1991) J Mol. Biol. 222:581-597; and Presta (2005) J. Allergy Clin. Immunol. 116:731.

The antibody of the present invention may include all forms of a chimeric antibody, a humanized antibody, a human antibody, and the like, comprising the above-described specific CDR constructs, and preferably a human antibody.

In addition, fragments of antibodies as used herein refer to fragments of antibodies that retain the antigen-specific binding ability of the whole antibody, and specifically include diabodies, Fab, Fab', F(ab)2, F(ab')2, Fv and scFv.

Fragment antigen-binding (Fab) is an antigen-binding fragment of an antibody, consisting of one variable domain and one constant domain in the heavy chain and light chain, respectively. F(ab')2 is a fragment produced by hydrolysis of antibody via pepsin, in which two Fabs are linked by a disulfide bond at the heavy chain hinge. F(ab') is a monomer antibody fragment in which a heavy chain hinge is added to a Fab obtained by reducing disulfide bonds of F(ab') 2 fragment. Fv (variable fragment) is an antibody fragment consisting of only variable regions of heavy chains and light chains, respectively. A single chain variable fragment (scFv) is a recombinant antibody fragment in which a heavy chain variable region (VH) and a light chain variable region (VL) are connected by a flexible peptide linker. A diabody is a fragment in which VH and VL of scFv are connected by a very short linker and do not bind to each other, while binding to VL and VH of other scFv of the same type to form a dimer.

The antibody or antigen-binding fragment thereof herein may be produced using methods known in the art, for example, phage display methods or yeast cell surface expression systems. The scFv may be prepared by the methods described in U.S. Pat. Nos. 4,946,778 and 5,258,498, while the methods described in WO 92/22324 or the like may be used for recombinant production of Fab, Fab 'and F (ab') 2 fragments.

The antibody of the present invention may be conjugated to enzymes, fluorescent materials, radioactive materials, and proteins, but are not limited thereto. Methods for conjugating the above materials to the antibody have been well known in the art.

The present invention provides a polynucleotide encoding the antibody or antigen-binding fragment thereof.

As used herein, the term 'polynucleotide' may be described as an oligonucleotide or a nucleic acid, and includes DNA molecules (e.g., cDNA or genomic DNA), RNA molecules (e.g., mRNA), DNA or RNA analogues thereof produced using nucleotide analogues (e.g., peptide nucleic acids and non-naturally occurring nucleotide analogues), and hybrids thereof. The polynucleotide may be single-stranded or double-stranded.

The sequence of the polynucleotide of the present invention is not particularly limited as far as it encodes the antibody or antigen-binding fragment thereof of the present invention. The polynucleotide encoding the antibody or antigen-binding fragment thereof according to an aspect of the present invention may be obtained by the methods known in the art. For example, the codon may be analyzed based on the amino acid sequence corresponding to the antibody full-length sequence of the present invention, or a part of the heavy chain and the light chain (particularly the region comprising the heavy chain variable region and the light chain variable region), and mRNA or cDNA may be constructed through these codon analysis. Such polynucleotides may be synthesized by oligonucleotide synthesis methods that are known in the art, for example, a polymerase chain reaction (PCR) method.

The present invention also provides a vector comprising the polynucleotide.

Such a vector is a recombinant expression vector. As used herein, the term 'recombinant' is compatible with ' genetic manipulation', and means the preparation of a type of a gene that does not exist in the natural state, using molecular cloning techniques such as transforming, cutting and connecting genes.

As used herein, the term 'expression' means that a protein or a nucleic acid is produced in a cell.

As used herein, the term 'recombinant expression vector' refers to a vector capable of expressing a target protein or nucleic acid (RNA) in a suitable host cells, and indicates a gene construct containing an essential regulatory element operatively linked to express a polynucleotide (gene) insert. The term 'operatively linked' refers to the functional linkage of a nucleic acid sequence encoding a target protein or RNA with its expression control sequence so as to perform its general functions. It means that a gene is linked in such a manner so that it can be expressed by an expression control sequences. The term "expression control sequence" refers to a DNA sequence that controls the expression of an operatively linked polynucleotide sequence in particular host cells. Such an expression control sequence includes a promoter for driving transcription, any operator sequence for controlling transcription, a sequence encoding a proper mRNA ribosomal binding site, a sequence for controlling the termination of transcription and translation, an initiation codon, a termination codon, a polyadenylation A signal, an enhancer and the like. Thus, a recombinant expression vector according to the present invention refers to a gene construct so operably linked that a polynucleotide encoding the antibody of the present invention having a unique CDR configuration capable of specifically binding to human NINJ-1 protein, as described above, is expressed in a suitable host cell.

The recombinant expression vector of the present invention is not particularly limited as long as it is a vector conventionally used in the field of cloning, and includes, for example, a plasmid vector, a cosmid vector, a bacteriophage vector, and a viral vector, but is not limited thereto. Specifically, the plasmid includes a plasmid derived from *Escherichia coli* (pBR322, pBR325, pUC118 and pUC119, pET-22b (+)), a plasmid derived from *Bacillus subtilis* (pUB110 and pTP5), and a plasmid derived from yeast (YEp13, YEp24 and YCp50), and the like, while the virus may be an animal virus such as retrovirus, adenovirus or vaccinia virus, an insect virus such as baculovirus, and pcDNA and the like.

The plasmid, which is a type of vector, means a linear or circular double-stranded DNA molecule to which external polynucleotide fragments can bind. Other forms of vectors may be viral vectors (e.g., replication defective retroviruses, adenoviruses and adeno-associated viruses), and as used herein, additional DNA fragments may be introduced into the viral genomes. Certain vectors are capable of performing autonomous replication in a host cell into which they are introduced (e.g., bacterial vectors including bacterial-origin vectors and episomal mammalian vectors). Other vectors (e.g., non-episomal mammalian vectors) are integrated into the genome of a host cell upon their introduction into the host cell, and thereby are replicated along with the host genome.

The polynucleotide encoding the heavy and light chains of the antibody or fragments thereof (particularly a antigen-binding fragment comprising a heavy chain variable region and a light chain variable region) of the present invention may be contained in different recombinant expression vectors or in one recombinant expression vector.

Meanwhile, the present invention provides a cell comprising the vector of the present invention. That is, the present invention provides a cell transformed with a recombinant expression vector comprising a polynucleotide encoding the antibody or antigen-binding fragment thereof according to the present invention.

As used herein, the cell (host cell) is not particularly limited as long as it is the cell that can be used to express the polynucleotide encoding the antibody or the antigen-binding fragment thereof contained in the recombinant expression vector of the present invention. The cells (host cells) transformed with a recombinant expression vector of the present invention may be prokaryotes (e.g., *E. coli*), eukaryotes (e.g., yeast or other fungi), plant cells (e.g., tobacco or tomato plant cells), animal cells (e.g., human cells, monkey cells, hamster cells, rat cells, mouse cells, insect cells) or hybridomas derived there from.

The prokaryotes suitable for the purpose of the present invention include, but are not limited to, gram negative or gram positive organisms, for example, Enterobacteriaceae, such as *Escherichia* (e.g., *E. coli*), *Enterobacter; Erwinia, Klebsiella, Proteus, Salmonella* (e.g., *Salmonella typhimurium*), *Serratia* (e.g., *Serratia marcescens*), and *Shigella*, as well as *Bacilli* (e.g., *B. subtilis* and *B. licheniformis*), *Pseudomonas* (e.g., *P. aeruginosa*), and *Streptomyces*. The cells of the present invention are not particularly limited as long as they can express the vector of the present invention, but preferably, *E. coli* for example, *E. coli* ER2537, *E. coli* B, *E. coli* X1776 (ATCC 31,537), *E. coli* W3110 (ATCC 27,325) or *E. coli* capable of expressing LacZ, but are not limited thereto, and more preferably *E. coli* ER2537.

The eukaryotes suitable for the purpose of the present invention include, but are not limited to, *Saccharomyces cerevisiae, Schizosaccharomyces pombe, Kluyveromyces* host, for example, *K. lactis, K. fragilis* (ATCC 12,424), *K. bulgaricus* (ATCC 16,045), *K. wickeramii* (ATCC 24,178), *K. waltii* (ATCC 56,500), *K. drosophllarum* (ATCC 36,906), *K. thermotolerans*, and *K. marxianus; Yarrowia* (EP 402, 226); *Pichia pastoris* (EP 183,070); *Candida; Trichoderma*

*reesia* (EP 244,234); *Neurospora crassa; Schwanniomyces*, for example, *Schwanniomyces occidentalis*; and filamentous fungi, for example, *Neurospora, Penicillium, Tolypocladium*, and *Aspergillus* hosts, for example, *A. nidulans* and *A. niger.*

Meanwhile, the cells according to the present invention may be animal cells, especially, vertebrate cells. The proliferation of vertebrate cells in culture (tissue culture) has become a routine procedure, and techniques therefor can be widely used. Examples of useful mammalian host cells may include monkey kidney CV1 line transformed with SV40 (COS-7, ATCC CRL 1651), human embryonic kidney line (293 or 293 cells subcloned for growth in suspension culture (Graham et al., 1977, J Gen Virol. 36: 59)), baby hamster kindey cells (BHK, ATCC CCL10), Chinese hamster ovarian cells/-DHFR (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kindey cells (CVI ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TRI cells (Mather et al., 1982, Annals NY. Acad. Sci. 383: 44-68), MRC 5 cells, FS4 cells, human hepatoma line (Hep G2), human embryonic kidney cell (HEK 293 cell), and Expi293F™ cells, but are not limited thereto, and may be preferably CHO cells, human embryonic kidney cells (HEK 293 cells) or Expi293F™ cells.

The cells provided in the present invention are cultured cells that can be transformed or transfected with the polynucleotide of the present invention or the vector containing the same, and subsequently, the polynucleotide or vector may be expressed in the host cells. The recombinant cells refer to cells that are transformed or transfected with a polynucleotide to be expressed.

The medium composition, culture conditions, culture time and the like for culturing the cells can be appropriately selected according to a method commonly used in the art. Commercially available media, such as Ham's F1O (Sigma-Aldrich Co., St. Louis, Mo.), minimum essential medium (MEM, Sigma-Aldrich Co.), RPMI-1640 (Sigma-Aldrich Co.), and Dulbecco's modified Eagle's medium (DMEM, Sigma-Aldrich Co.), may be suitable for cell culture. The media may further contain, if necessary, hormones and/or other growth factors, salts, buffers, nucleotides, antibiotics, trace elements, and glucose or equivalent energy sources thereof.

Meanwhile, the present invention provides a method for preparing an antibody or a antigen-binding fragment thereof that specifically binds to a human NINJ-1 protein, the method comprising the steps of:

culturing the cell under the condition that a polynucleotide is expressed, thereby producing a polypeptide comprising a light chain variable region and a heavy chain variable region; and recovering a polypeptide from the cell or a medium in which the cell has been cultured The cells in the above preparation method are described above, which contain a polynucleotide encoding the antibody or antigen-binding fragment thereof according to the present invention. As described above, since the antibody or antigen-binding fragment thereof of the present invention has an amino acid sequence of an important region for antigen recognition and binding (CDRs and variable regions containing the same), the antibody of the present invention can be easily and repetitively mass produced by those skilled in the art.

The polypeptide in the preparation method according to an aspect of the present invention may be the antibody or antigen-binding fragment thereof, per se, of the present invention, while other amino acid sequences, besides the antibody or antigen-binding fragment thereof of the present invention, may be further added to the polypeptide. In these cases, the additionally added amino acids may be removed from the antibody or antigen-binding fragment thereof of the present invention by using methods that are well known to a person skilled in the art.

The culture may vary in medium composition and culture conditions depending on the type of the cells, while conditions for expressing the polynucleotide according to the cell may be appropriately selected and controlled by a person skilled in the art. The above-mentioned examples may be referred to in connection with the cell culture medium of the present invention.

The antibody molecules may be accumulated in the cellular cytoplasm, secreted from cells, or targeted into the periplasm or extracellular medium (supernatant) by appropriate signal sequence. Preferably, the antibody molecules are targeted into the periplasm or extracellular medium. In addition, preferably, the produced antibody molecules are refolded by methods that are well known to a person skilled in the art so that the antibody molecules have functional conformations. Further, in the case of producing an IgG type antibody, the heavy chain and the light chain may be expressed in separate cells, while preparing a complete antibody by contacting the heavy chain with the light chain in a separate step. The heavy chain and the light chain may be expressed in the same cell to form a complete antibody inside the cell.

The collection of the polypeptide may vary according to the characteristics of the produced antibody or antigen-binding fragment thereof, characteristics of the cells expression patterns, the existence of targeting and the like, and may be appropriately selected and controlled by a person skilled in the art. For example, an antibody or antigen-binding fragment thereof secreted into a culture medium may be obtained by obtaining a host cell-cultured medium, and recovering the antibody by such a method as filtration (such as ultrafiltration) or centrifugation to remove impurities. If necessary, in order to release and recover the antibody present in specific intracellular organelles or cytoplasm outside of the cell, the cells may be dissolved in an amount that does not affect the functional structure of the antibody or the antigen-binding fragment thereof. Further, in order to remove impurities the obtained antibody may be further subjected to chromatography, filtration by a filter or the like, dialysis or the like, followed by concentration. To inhibit proteolysis, a protease inhibitor, such as PMSF, may be included in any preceding step, while antibiotics may be included to prevent the growth of accidental contaminants.

Antibodies prepared from cells may be purified by using, for example, hydroxyapatite chromatography, gel electrophoresis, dialysis, and affinity chromatography.

The antibody or antigen-binding fragment thereof of the present invention specifically binds to human NINJ-1, and thus is useful for example in the diagnostic analysis for detecting and quantifying the existence (or expression) of the human NINJ-1 protein in particular cells, tissues, or serum. As used herein, the term 'analysis' may preferably mean 'measurement'. Qualitative analysis may refer to the measurement and confirmation of the presence or absence of a target substance. Quantitative analysis may refer to measure and identify the presence level (expression level) or a change thereof in the amount of the target substance. Herein, the analysis or measurement can be performed without limitation, including both qualitative and quantitative methods.

Therefore, the present invention provides a method of specifically detecting human NINJ-1, the method comprising the steps of:

contacting the antibody or a antigen-binding fragment thereof with a sample; and detecting the antibody or antigen-binding fragment thereof.

In order to "detect" the antibody or antigen-binding fragment thereof, the antibody or fragment thereof may be generally labeled with a detectable moiety.

For example, the antibody or antigen-binding antigen-binding fragment thereof may be labeled with radioisotopes or fluorescent labels using the techniques described in Current Protocols in Immunology, Volumes 1 and 2, 1991, Coligen et al., Ed. Wiley-Interscience, New York, N.Y., Pubs. Radioactivity may be measured by, for example, scintillation counting, while the fluorescence may be quantified using a fluorometer.

In addition, various enzyme-substrate labels may be utilized. Exemplary enzymatic labels include *luciferase* (such as *drosophila luciferase* and bacterial *luciferase* (U.S. Pat. No. 4,737,456)), luciferin, 2,3-dihydrophthalazinediones, malate dehydrogenase, urase, peroxidase (such as horseradish peroxidase (HRPO)), alkaline phosphatase, β-galactosidase, glucoamylase, lysozyme, saccharide oxidase (e.g., glucose oxidase, galactose oxidase, and glucose-6-phosphate dehydrogenase), heterocyclic oxidase (e.g., uricase and xanthine oxidase), lactoperoxidase, microperoxidase, and the like. The conjugation of the enzyme to the antibody is preferably described in O'Sullivan et al., 1981, Methods for the Preparation of Enzyme-antibody Conjugates for use in Enzyme Immunoassay, in Methods in Enzyme (J. Langone & H. Van Vunakis, eds.), Academic press, N. Y., 73: 147-166).

The labels may be indirectly conjugated to antibodies using various known techniques. For example, the antibody may be conjugated to biotin, and any labels pertaining to three classes of widespread categories cited above may be conjugated to avidin or vice versa. Biotin may selectively bind to avidin, and therefore, this label may be conjugated to the antibody in such an indirect manner. Alternatively, in order to attain the indirect conjugation of a label to an antibody, the antibody may be conjugated to small hapten (e.g., digoxin), and one of different types of labels recited above may be conjugated to the anti-hapten antibody (e.g., anti-digoxin antibody), resulting in the indirect conjugation of the label to the antibody.

The antibody or antigen-binding fragment thereof of the present invention may be used by any known analysis method, such as competitive binding analysis, direct and indirect sandwich analysis, and immunoprecipitation analysis. Specifically, herein, the method for detecting the antibody or the antigen-binding fragment thereof is not particularly limited as long as it is a detection method using an antibody in the art. For example, the detection method may use one of the group consisting of Western blotting or enzyme-linked immunospecific assay (ELISA), radioimmunoassay, radioimmunoprecipitation, Ouchterlony immunodiffusion, rocket immunoelectrophoresis, Immunostaining (Including immunohistochemical staining and immunofluorescence staining), immunoprecipitation assay, complement fixation assay, Fluorescence activated cell sorter (FACS) or protein-chip method.

The antibody or antigen-binding fragment thereof of the present invention may be used for a diagnostic kit, that is, a diagnostic kit for performing diagnostic analysis, which is a combination of reagents packaged in predetermined amounts together the operation manual. If the antibody is labeled with an enzyme, the kit may contain a substrate and a cofactor as a substrate precursor providing a chromophore or a fluorophore, which is required by the enzyme. The kit may also contain other additives, such as a stabilizer and a buffer (e.g., block buffer or lysis buffer). The relative amounts of various reagents may be widely varied in order to provide the concentrations of the reagents in a solution to sufficiently optimize the sensitivity of analysis. The reagents may be provided as a generally freeze-dried or dried powder, including a vehicle, by which a reagent solution having an appropriate concentration is provided when the reagents are dissolved.

It is known that the NINJ-1 level is up-regulated in patients with multiple sclerosis. Thus, it has been known that NINJ-1 can be used as a diagnostic marker for diagnosis, disease progression, and prognosis assessment before and after treatment of multiple sclerosis. That is, diagnosis and prognostic evaluation of multiple sclerosis can be performed by detecting NINJ-1 protein in a biological sample. Thus, the human NINJ-1 specific detection method of the present invention may be used as a method of providing information necessary for multiple sclerosis diagnosis by measuring the expression level of the human NINJ-1 in a sample collected from a potential patient.

The biological sample includes blood and other liquid samples having biological origins, biopsy samples, solid tissue samples such as tissue culture, or cells derived therefrom. More specifically, examples of the biological sample may include, but are not limited to, tissues (especially, neurological tissues), extracts, cell lysates, whole blood, plasma, serum, saliva, ocular fluid, cerebrospinal fluid, sweat, urine, milk, ascites fluid, synovial fluid, peritoneal fluid, and the like. The sample may be obtained from animals, preferably mammals, and most preferably humans. The sample may be pre-treated before its use for detection. For example, the sample may be pre-treated by filtration, distillation, extraction, concentration, inactivation of interfering components, reagent addition, and the like. In addition, nucleic acid and proteins isolated from the sample may be used for detection. The detection is described as above.

On the other hand, the binding of immune cells to the epithelial cells of central nervous system and the migration of immune cells into the central nervous system are an important pathology in multiple sclerosis, and therapeutic strategies for preventing such binding and migration have been used in the treatment of existing multiple sclerosis (for example natalizumab, etc.). It is known in the art that NINJ-1 acts as an adhesion molecule in the binding of immune cells to the epithelial cells of central nervous system and migration of the immune cells into the central nervous system. Therefore, if the binding of immune cells to central nervous system endothelial cells and migration of the immune cells is inhibited by suppressing the activity of NINJ-1, the prevention and treatment of multiple sclerosis can be achieved. Accordingly, the present inventors found that the antibody of the present invention significantly inhibits the adhesion between the immune cell line and human cerebral endothelial cells, thus confirming its preventive and therapeutic effects of multiple sclerosis.

Therefore, the present invention provides a pharmaceutical composition for preventing or treating multiple sclerosis, the composition comprising the antibody or antigen-binding fragment thereof as an active ingredient.

The present invention also provides a pharmaceutical composition for preventing or treating a multiple sclerosis, the composition consisting of the antibody or antigen-binding fragment thereof as an active ingredient.

Further, the present invention provides a pharmaceutical composition for preventing or treating a multiple sclerosis, the composition consisting essentially of the antibody or antigen-binding fragment thereof as an active ingredient.

In addition, the present invention provides use of the antibody or a antigen-binding fragment thereof for the preparation of an agent for the prevention and treatment of multiple sclerosis The present invention also provides a method for preventing and treating multiple sclerosis in a subject, the method comprising administering an effective amount of a composition comprising the antibody or antigen-binding fragment thereof as an active ingredient to a subject in need thereof.

Further, the present invention provides a method for preventing and treating multiple sclerosis in a subject, the method comprising administering an effective amount of a composition consisting of the antibody or antigen-binding fragment thereof as an active ingredient to a subject in need thereof.

Further, the present invention provides a method for preventing and treating multiple sclerosis in a subject, the method comprising administering an effective amount of a composition consisting essentially of the antibody or antigen-binding fragment thereof as an active ingredient to a subject in need thereof.

Multiple sclerosis (MS) is one of the demyelinating diseases of the central nervous system and is a chronic inflammatory disease mainly occurring in a young age group. The cause of multiple sclerosis is the disappearance of the myelin sheath surrounding the axon of the nerve cell, which may lead to a failure of neural transmission, resulting in neurological symptoms. When the myelin sheath is lost, scarring or sclerosis occurs. In addition, although myelin sheath abnormalities are known to occur due to autoimmunity, genetic factors and the like, viral infections, environmental factors, the exact cause of multiple sclerosis has not yet been determined. In the present invention, multiple sclerosis includes relapsing remitting multiple sclerosis (RRMS), secondary-progressive multiple sclerosis (SPMS), primary progressive multiple sclerosis (PPMS), and progressive-relapsing multiple sclerosis (PRMS).

In addition, the antibody or antigen-binding fragment thereof of the present invention has an effect of preventing or treating cancer by inhibiting cancer metastasis. Therefore, the present invention provides a pharmaceutical composition for inhibiting cancer metastasis and preventing or treating cancer, the composition comprising the antibody or antigen-binding fragment thereof as an active ingredient.

The present invention also provides a pharmaceutical composition for inhibiting cancer metastasis and preventing or treating cancer, the composition consisting of the antibody or antigen-binding fragment thereof.

Further, the present invention provides a pharmaceutical composition for inhibiting cancer metastasis and preventing or treating cancer, the composition consisting essentially of the antibody or antigen-binding fragment thereof.

An embodiment according to another aspect of the present invention provides use of the antibody or a antigen-binding fragment thereof for the preparation of an agent for inhibiting cancer metastasis and preventing or treating of cancer An embodiment according to another aspect of the present invention provides a method for inhibiting cancer metastasis and preventing and treating cancer in a subject, the method comprising administering an effective amount of a composition comprising the antibody or fragment thereof as an active ingredient to a subject in need thereof.

The present invention also provides a method for inhibiting cancer metastasis and preventing and treating cancer in a subject, the method comprising administering an effective amount of a composition consisting of the antibody or antigen-binding fragment thereof as an active ingredient to a subject in need thereof.

Further, the present invention provides a method for inhibiting cancer metastasis and preventing and treating cancer in a subject, the method comprising administering an effective amount of a composition consisting essentially of the antibody or antigen-binding fragment thereof as an active ingredient to a subject in need thereof.

The antibody or pharmaceutical composition comprising the antibody of the present invention or a pharmaceutical composition comprising the sane inhibits metastasis of tumor cells and thus can be applied to various cancers. For example, the cancer, which is not limited to, is selected from the group consisting of colon cancer, lung cancer, liver cancer, gastric cancer, esophageal cancer, pancreatic cancer, gallbladder cancer, renal cancer, bladder cancer, prostate cancer, testiscular cancer, cervical cancer, endometrial cancer, choriocarcinoma, ovarian cancer, breast cancer, thyroid cancer, brain cancer, head and neck cancer, malignant melanoma, lymphoma, and aplastic anemia.

The pharmaceutical composition according to the present invention may comprise the antibody or antigen-binding fragment thereof of the present invention alone, or may further comprise at least one pharmaceutically acceptable carrier. The term "pharmaceutically effective amount" as used herein refers to an amount that shows more effective reactions compared with a negative control group, and preferably refers to an amount sufficient to treat cancer.

The term "pharmaceutically acceptable" composition refers to a non-toxic composition that is physiologically acceptable, does not inhibit an action of an active ingredient when administered to humans, and does not usually induce an allergic reaction or similar reactions, such as gastroenteric troubles and dizziness.

In the pharmaceutical composition according to the present invention, the antibody or antigen-binding fragment thereof may be administered in various forms of oral and parenteral administration at the time of clinical administration. In the case of formulation, it may be prepared by using diluents or excipients such as fillers, extenders, binders, humectants, disintegrants, surfactants and the like which are usually used.

For example, it can be formulated into an injection as a formulation for parenteral administration. The injection needs to be essentially sterilized, and needs to be protected from the contamination of microorganisms, such as bacteria and fungus. Examples of the suitable carrier for the injection may include, but are not limited to, solvents or dispersion media, including water, ethanol, polyols (e. g., glycerol, propylene glycol, liquid polyethylene glycol, etc.), mixtures thereof, and/or vegetable oils. More preferably, Hanks' solution, Ringer's solution, phosphate buffered saline (PBS) or sterile water for injection containing triethanolamine, or an isotonic solution (such as 10% ethanol, 40% propylene glycol, or 5% dextrose) may be used as a suitable carrier. In order to protect the injection from microbial contamination, the injection may further contain various antibiotic and antifungal agents, such as paraben, chlorobutanol, phenol, sorbic acid, and thimerosal. In most cases, the injection may further contain an isotonic agent, such as sugar or sodium chloride. These formulations and other pharmaceutically acceptable carriers may be those described in the literature (Remington's Pharmaceutical Science, 15th Edition, 1975, Mack Publishing Company, Easton, Pa.), which is a commonly known form of pharmaceutical chemistry.

A total effective amount of the pharmaceutical composition of the present invention may be administered to a patient in a single dose, or in a multiple dose for a long period of time by a fractionated treatment protocol. In addition, the content of the active ingredient may be varied depending on the purpose of administration. The effective dose is determined in consideration of various factors, such as route of administration, number of administration, patient's age, body weight, health condition, and sex, severity of disease, food, and excretion rate. Therefore, considering these various factors, a person skilled in the art could determine the appropriate effective dose depending on the purpose of administration. It may also be determined by monitoring the efficacy of the therapy using a well-known in vivo assay or an assay that determines the activity of immune cells, after administering the antibody or antigen-binding fragment thereof according to the present invention. The pharmaceutical composition according to the present invention is not particularly limited to any dosage form, route of administration, and administration method thereof as long as the composition shows the effects of the present invention.

As used herein, the "effective amount" refers to an amount showing effects in alleviating, treating, and preventing the diseases described above upon its administration to a subject. The "subject" may be an animal, preferably a mammal, especially an animal including a human being, and may be cells, tissues, organs, or the like originated from an animal. The subject may be a patient requiring the said effects.

As used herein, the term, 'composition' or 'agent' may be in the form of a food composition, a cosmetic composition, a pharmaceutical composition and the like, preferably a pharmaceutical composition, as described above. The composition herein may comprise from 0.001% to 99.999% by weight of the antibody of the invention and from 99.999% to 0.001% by weight of a suitable carrier, which may contain suitable additives.

The term "comprising" is used synonymously with "containing" or "being characterized", and does not exclude additional ingredients or steps that are not mentioned in the compositions and the methods. The term "consisting of" excludes additional elements, steps, or ingredients that are not separately described. The term "consisting essentially of" means that in the scope of the compositions or methods, the term includes any material or step that does not substantially affect basic characteristics of the compositions or methods, as well as described materials or steps.

Advantageous Effect

Accordingly, the present invention provides an antibody or antigen-binding fragment thereof that specifically binds to a human-derived Ninjurin-1 (NINJ-1) protein. The antibody or antigen-binding fragment thereof according to the present invention has a significantly high binding affinity and specificity to human NINJ-1 and does not show a cross-reactivity with other origin-derived NINJ-1 proteins (especially, mouse NINJ-1 protein) having high protein similarity. Thus, it provides significant advantages not only in the diagnosis of diseases related to NINJ-1 protein, but also in the accuracy, high sensitivity and the like in inhibiting the pathological conditions involved in NINJ-1 protein. In particular, the antibody provided by the present invention is remarkably effective in inhibiting adhesion between immune cells and human cerebral endothelial cells, and thus has a therapeutic effect on multiple sclerosis.

BRIEF DESCRIPTION OF DRAWINGS/FIGURES

Figure 5:
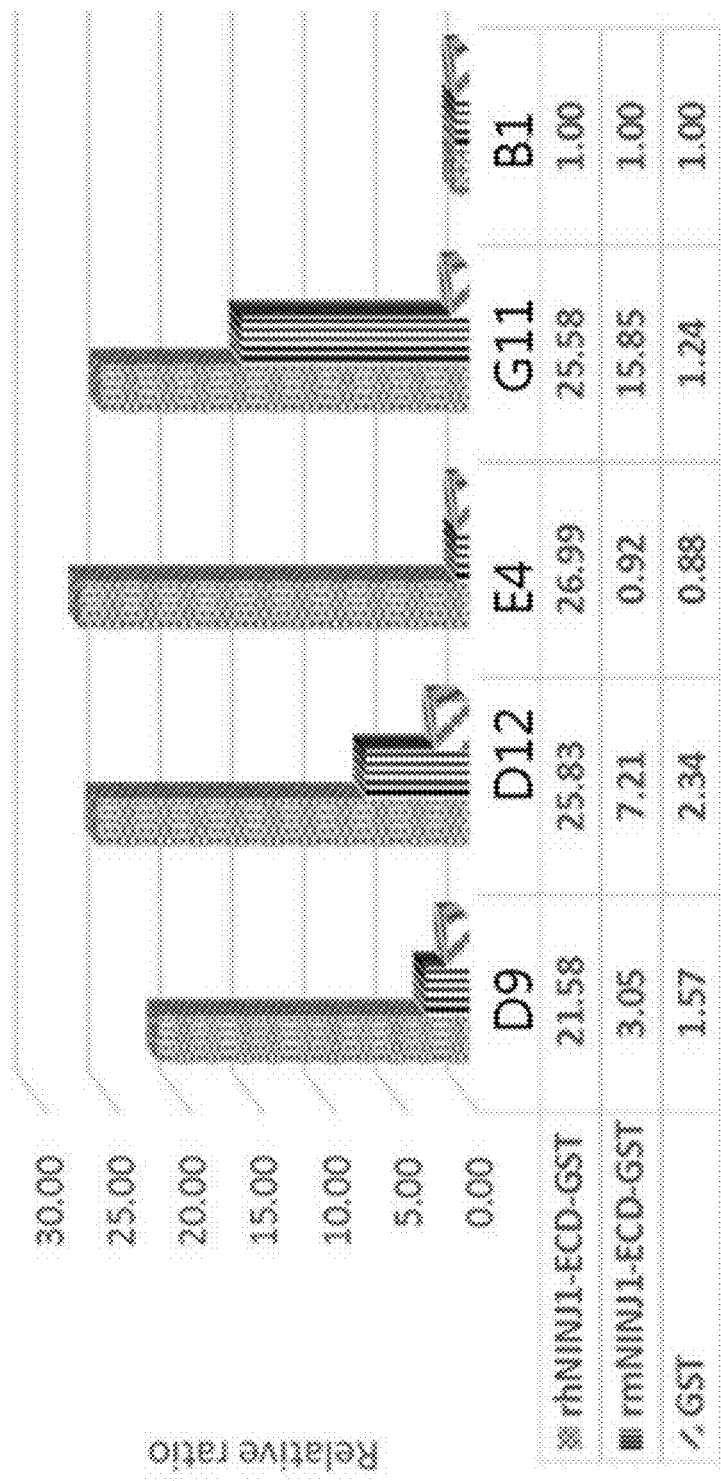

FIG. 5 is a result of final selection of four affinity groups (D9, D12, E4 and G11) having high affinity to GST/HuN-INJ-1 and GST/musNINJ-1 among candidates showing affinity to HBAg1, showing comparatively affinity to GST (Control), GST/huNINJ-1, GST/musNINJ-1 represented by each antibody (The absorbance value at 430 nm indicated by each candidate group was normalized to the value of B1 (Non-binding active control)).

FIG. 6 is a schematic diagram showing a process for producing an IgG expression vector containing an antibody heavy chain variable region (VH) or an antibody light chain variable region (VL) of scFv.

Figure 7A:
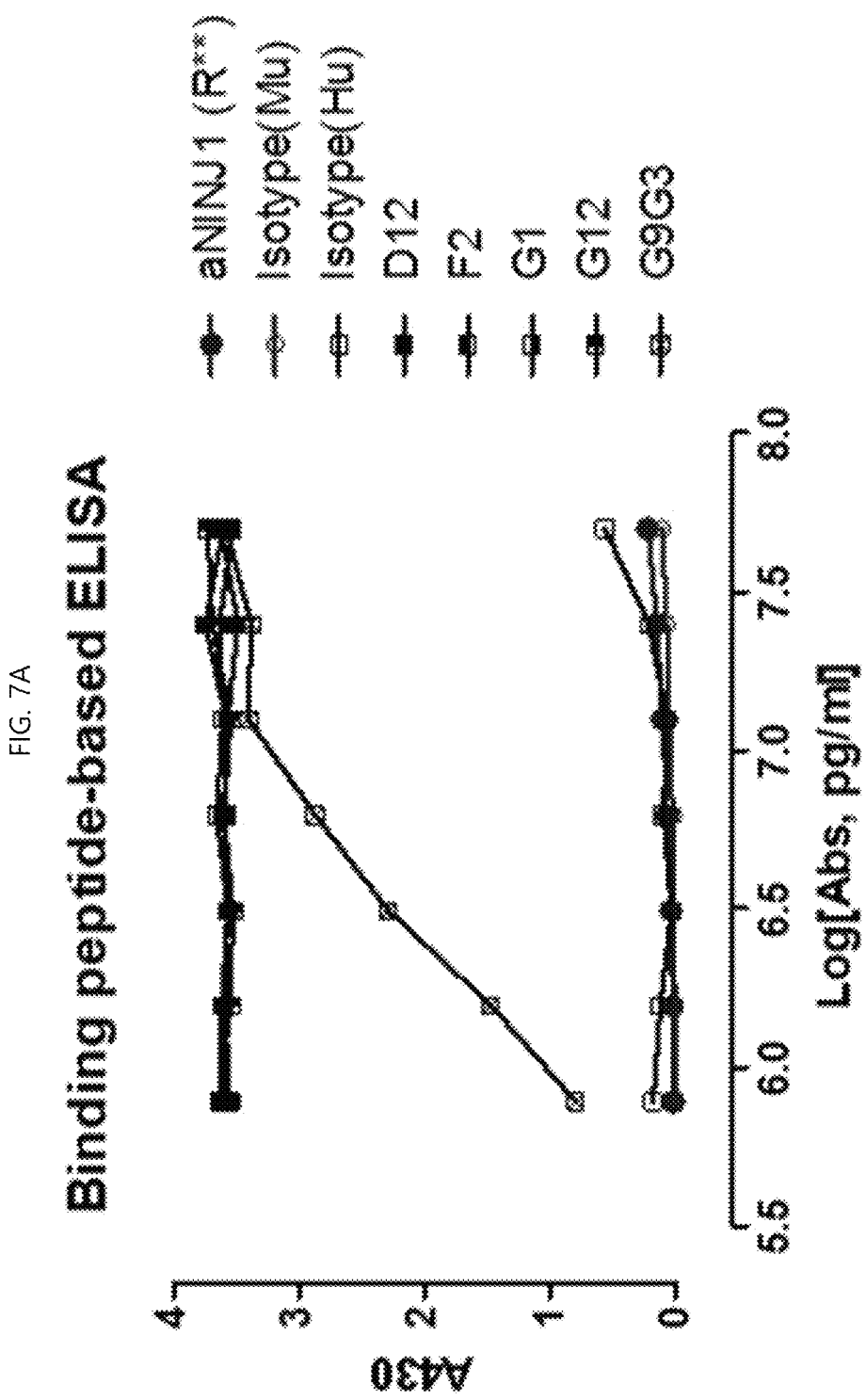
Figure 7B:
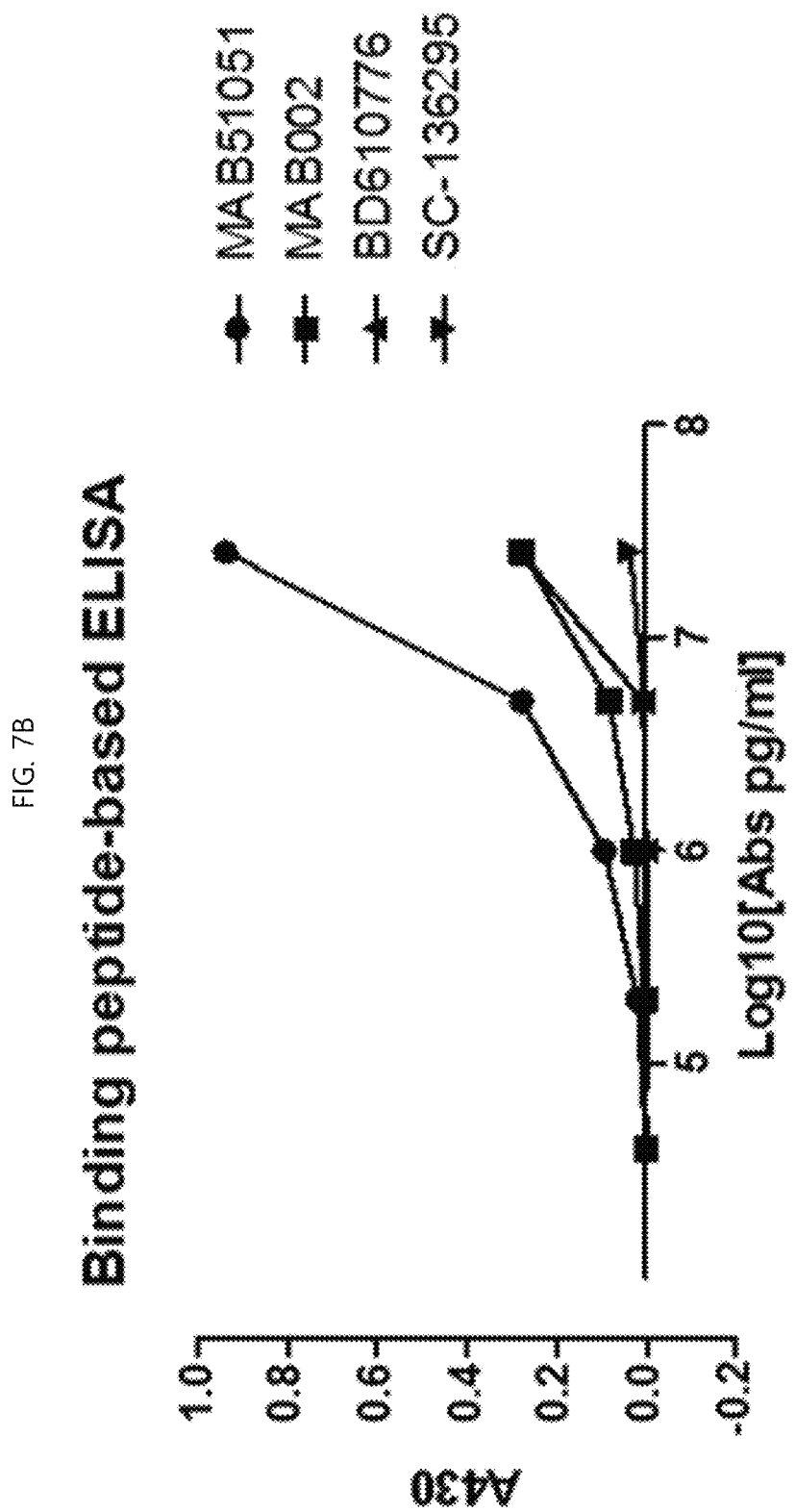

FIG. 7 shows comparative results regarding the affinity of each test group antibody to HBAg1 (P26-N37 region) verifying that, a D12 Ig antibody of the present invention (FIG. 7a) has a significantly higher affinity for HBAg than the anti-NINJ-1 antibodies (FIG. 7a, FIG. 7b) sold by other companies.

Figure 8A:
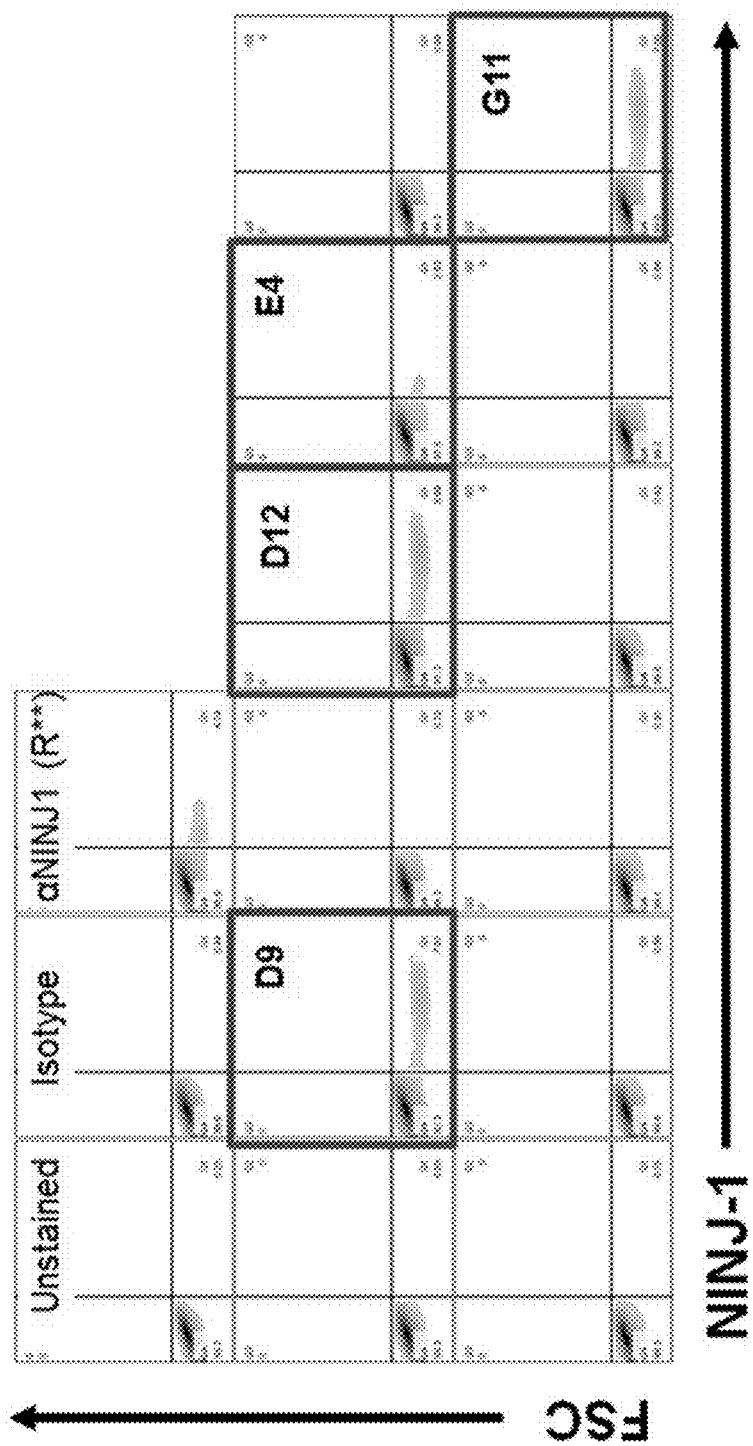

FIG. 8a shows comparative results regarding that the D9, D12, E4 and G11 Ig antibody of the present invention among the various candidate groups have a very high specificity in binding to native human NINJ-1 protein expressed in normal cells.

Figure 8B:
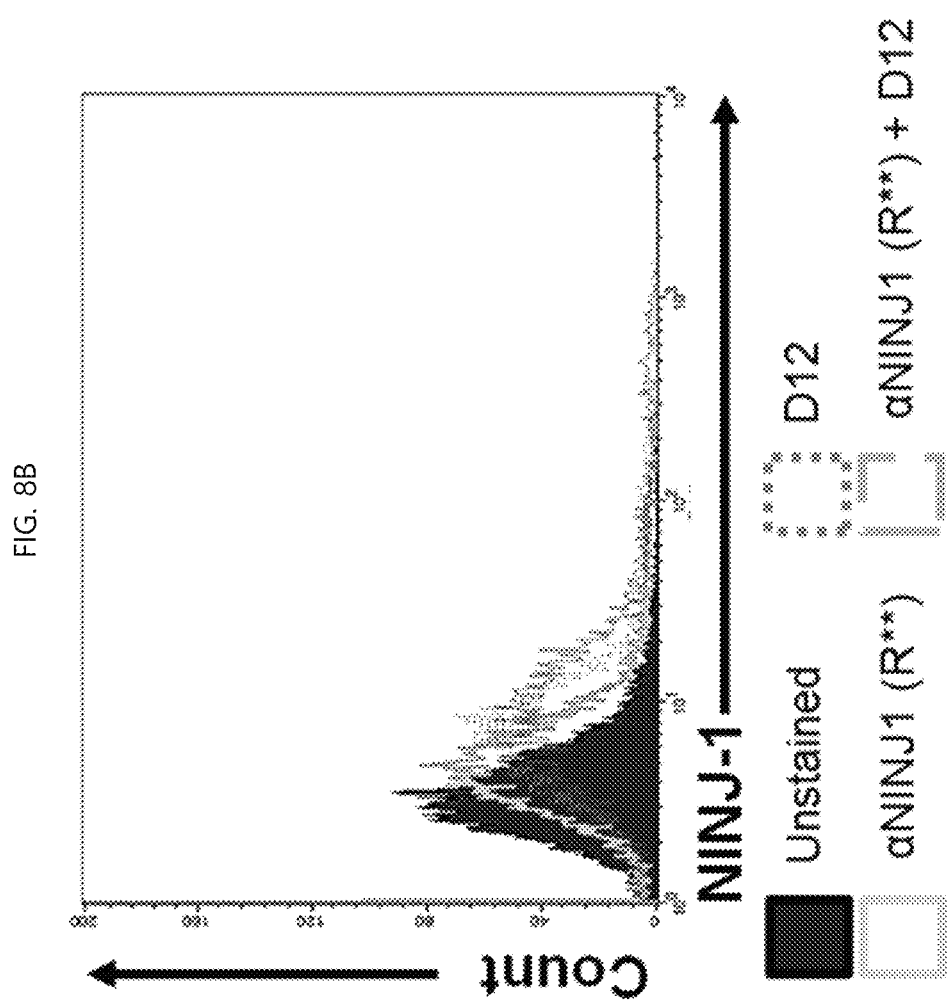

FIG. 8B shows results confirming that the D12 Ig antibody of the present invention does not share an antigen recognition site with an anti-NINJ-1 antibody (R&D systems, Cat No. MAB51051, labeled R**) available from other companies.

Figure 9A:
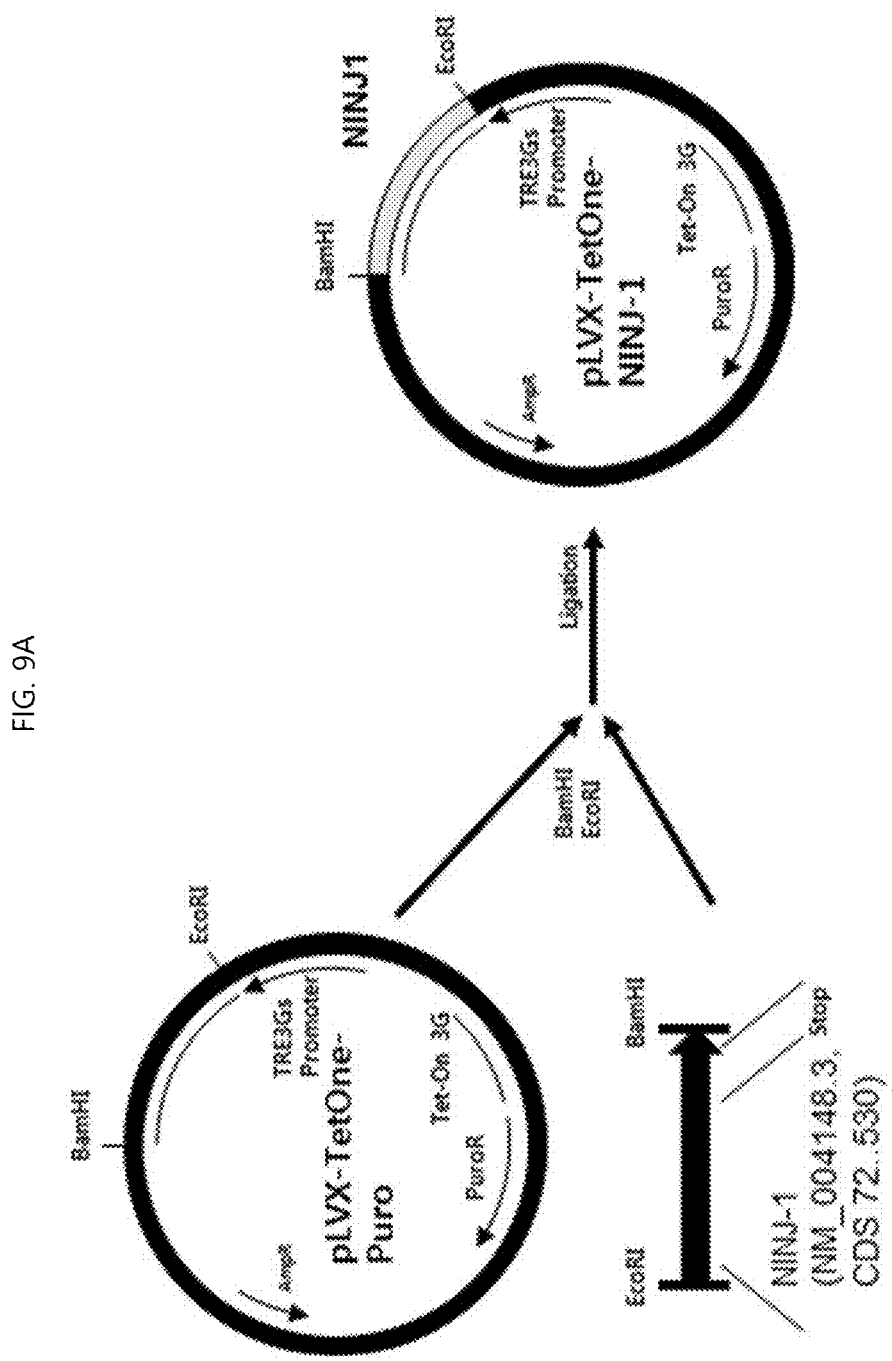

FIG. 9a is a schematic diagram showing a procedure for obtaining a recombinant vector for the production of a doxycycline-inducible human NINJ-1 overexpressing glioblastoma cell line.

Figure 9B:
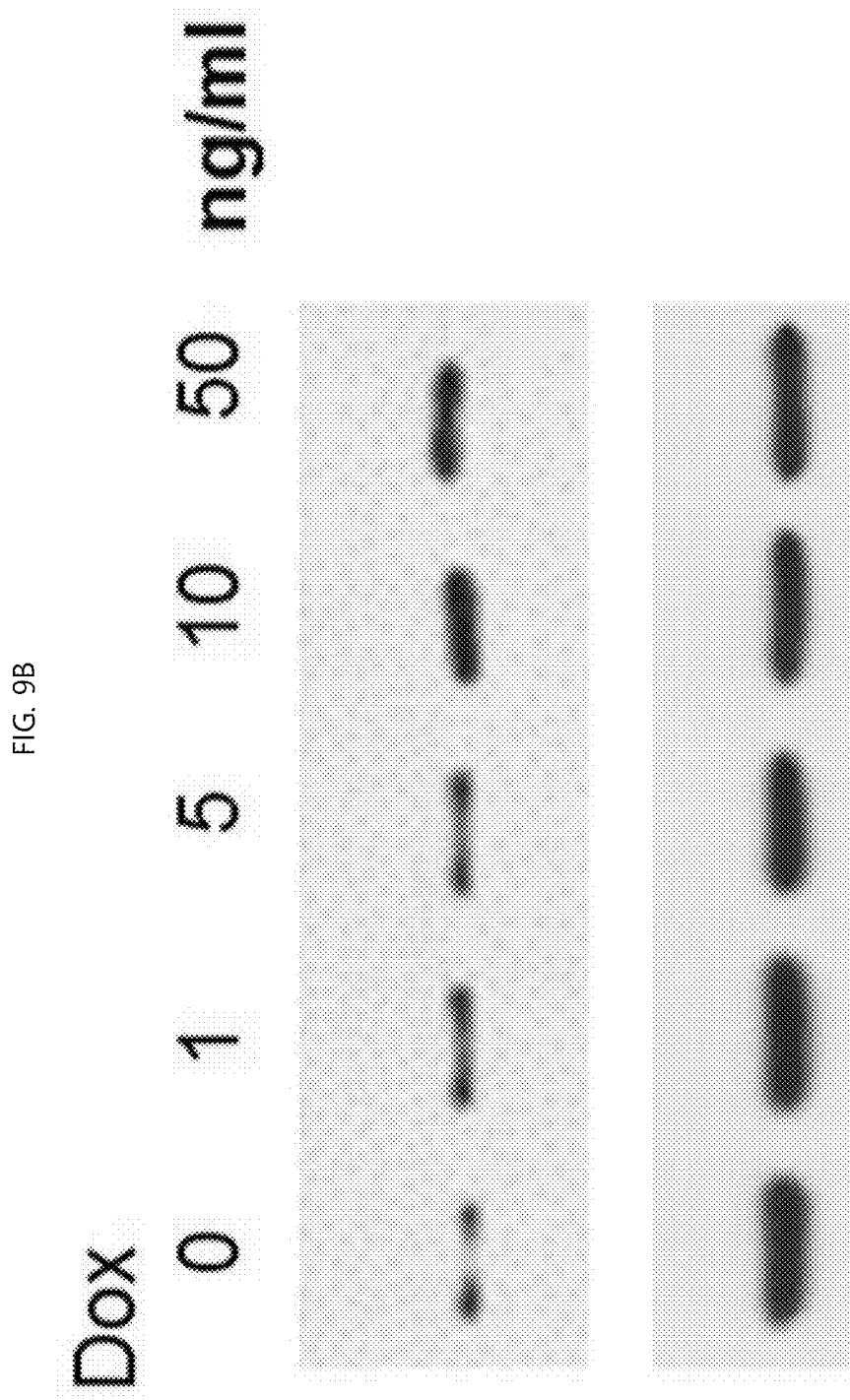

FIG. 9b shows the result of Western blotting detecting the expression level of the human NINJ-1 in the U87MG pLVX NINJ-1 glioblastoma cell line according to the treatment concentration of doxycycline.

Figure 10:
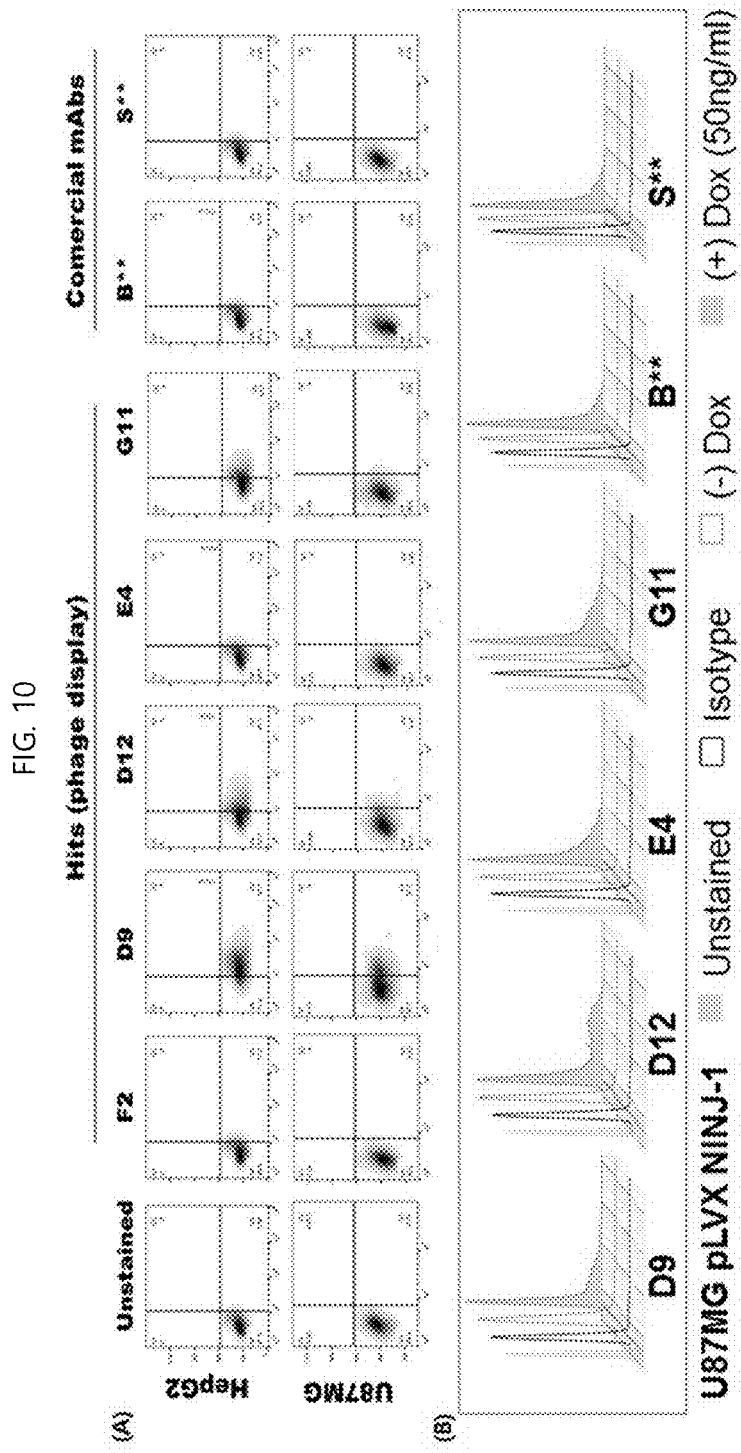

FIG. 10 shows the results of comparing the affinity of the D9, D12 E4 and G11 Ig antibody of the present invention and the two kinds of anti-NINJ-1 antibodies (BD bioscience Cat No. BD610776 (labeled B), and SantaCruz Cat No. sc-136295 (labeled S)) against the human NINJ-1 protein expressed in the U87MG pLVX NINJ-1 glioblastoma cell line.

Figure 11:
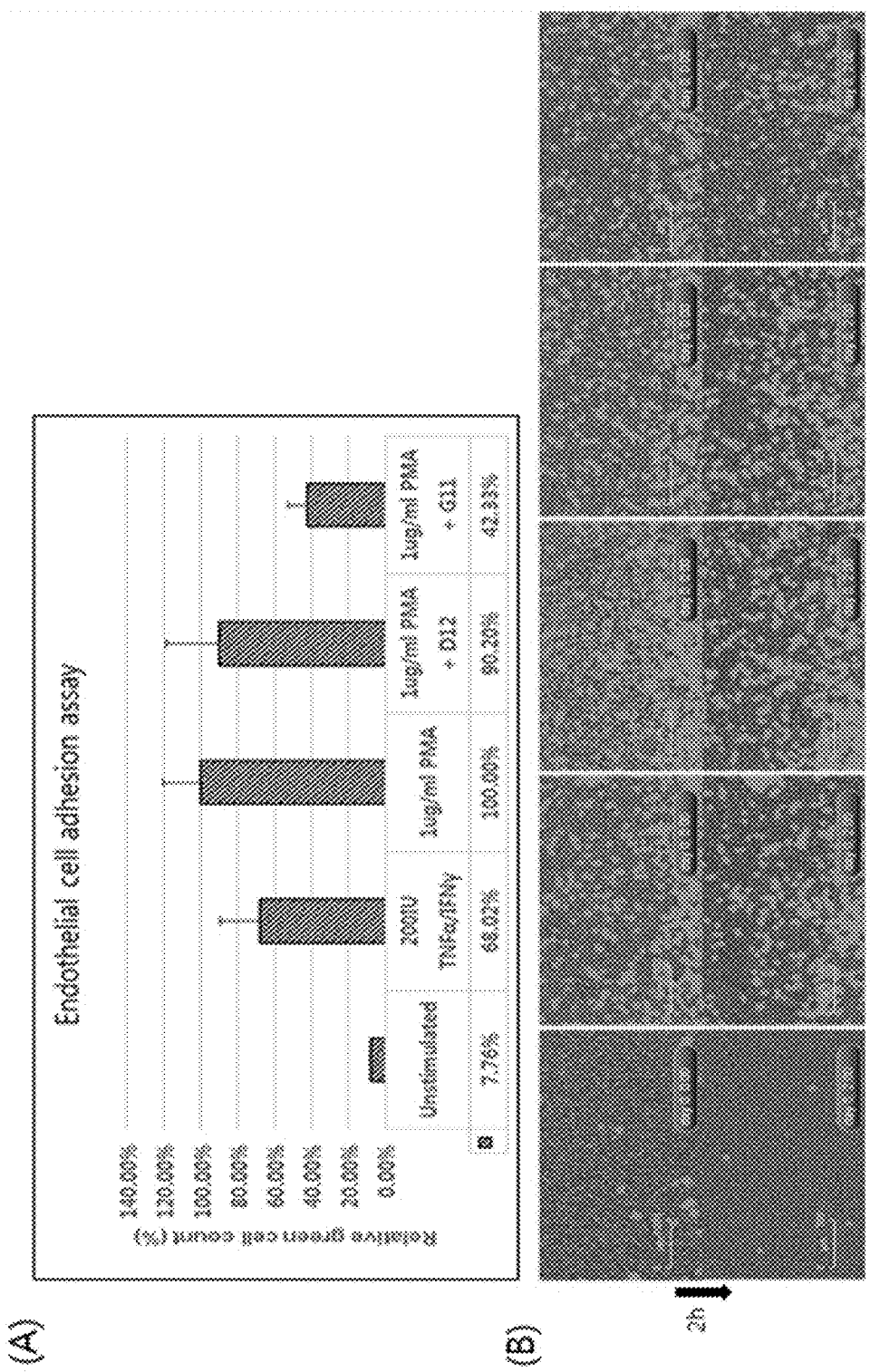

FIG. 11 shows results confirming whether the D9, D12, E4 and G11 Ig antibody of the present invention inhibits the adhesion between the immune cells and the human cerebral endothelial cells in order to confirm whether or not the antibody has utility as a therapeutic agent for multiple sclerosis.

MODE FOR CARRYING OUT INVENTION

Hereinafter, the present invention will be described in detail.

However, the following examples are only illustrative of the present invention, and the present invention is not limited to the following examples.

EXAMPLE 1

Identification of Antibodies Using P26-N37 Region of Human NINJ-1 Protein 1-1. Bio-Panning In order to identify antibodies specific to the P26-N37 region of human NINJ-1 (Ninjurin-1, SEQ ID NO: 25), the following experiment was performed using phage display technology based on the human scFv library. The fragment peptide for the P26-N37 region is hereinafter referred to as HBAg1.

Biotin-conjugated peptides at the ends of HBAg1 were synthesized, followed by binding to Dynabeads M-270 streptavidin (GE Healthcare Life Science). Subsequently, the scFv phage of the library was reacted at 37° C. for 1 hour and 30 minutes.

Then, the scFv phage having the specific binding was obtained and infected (input) with ER2537 *E. coli* (NEB) cultured to be 0.5 to 0.7 at OD600, and then ancillary phages were added and cultured in solid medium at 37° C. for 12 to 16 hours. For some, shake culture was performed in liquid medium at 37° C. and 160 rpm for 12 to 16 hours. Thereafter, the number of colony on the solid medium was measured and the output was confirmed. Poly ethylene glycol (PEG, Sigma aldrich) was added to the culture solution to precipitate the phage, and the same experiment was further repeated two more times to perform final third round of panning.

Figure 1:
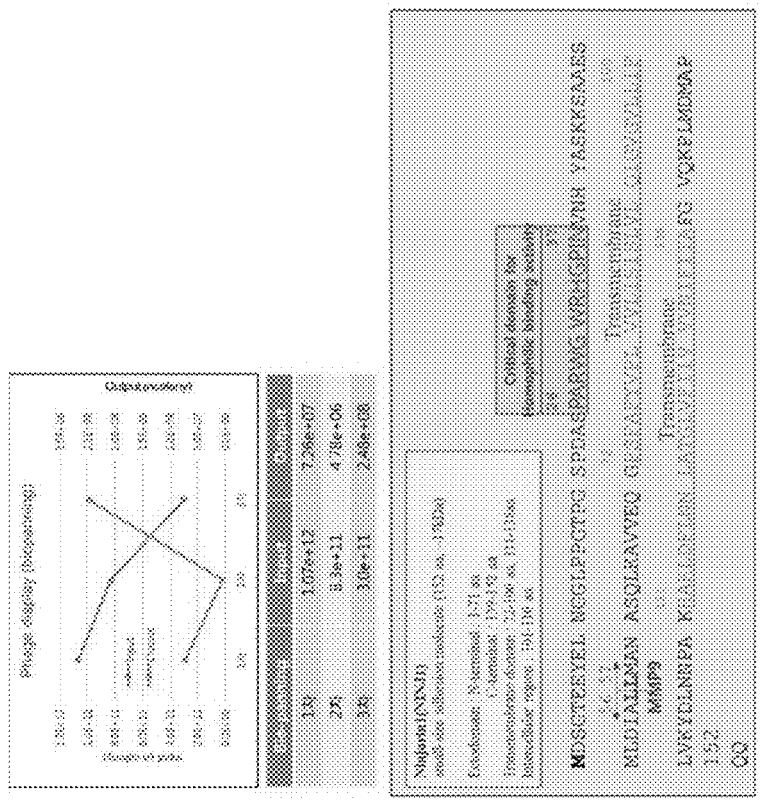
FIG. 1 shows each domain and a domain important for homologous binding ability in the human NINJ-1 (Ninjurin-1) protein sequence (SEQ ID NO: 25), and shows the number of colonies by each time during the bio-panning process using the antigen corresponding to the homologous binding domain.

The number of colony of the phage decreased in the second round compared to the first round, whereas it increased in the third round. This result is shown in FIG. 1.

1-2. Selection of Human NINJ-1 scFv Candidates

After the host cells (ER2537, NEB) were infected with the phage recovered in the 3rd bio-panning of Example 1-1, 95 colonies were selected on LB solid medium, and then cultured in liquid medium at 700 rpm at room temperature.

Then, each well was treated with Isopropyl B-D-1-thiogalactopyranoside (IPTG) to a final concentration of 1 mM, and cultured at 30° C. for 12-16 hours at 200 rpm. The culture solution was centrifuged at 3,000 rpm for 20 minutes to remove the supernatant, and osmotic cell lysis was performed through TES buffer to obtain intracellular phage particles. The plate was coated with HBAg1 or Phosphate buffered saline (PBS, control) at a concentration of 10 ug/ml in a 96-well plate (Thermo scientific, Cat No. 436014) previously coated with streptavidin, and each 50 μl of recovered phage particles was added to the coated plate, followed by reaction at room temperature for 1 hour. Then, the anti-HA (hemagglutinin) secondary antibody (Santa cruz biotechnology) conjugated with horseradish peroxidase was added and reacted again at room temperature for 1 hour. Then, a color development reaction using the TMB solution was induced for 5 minutes, and the reaction was stopped with 1N $H_2SO_4$ solution, and the absorbance was measured at 430 nm.

Figure 2:
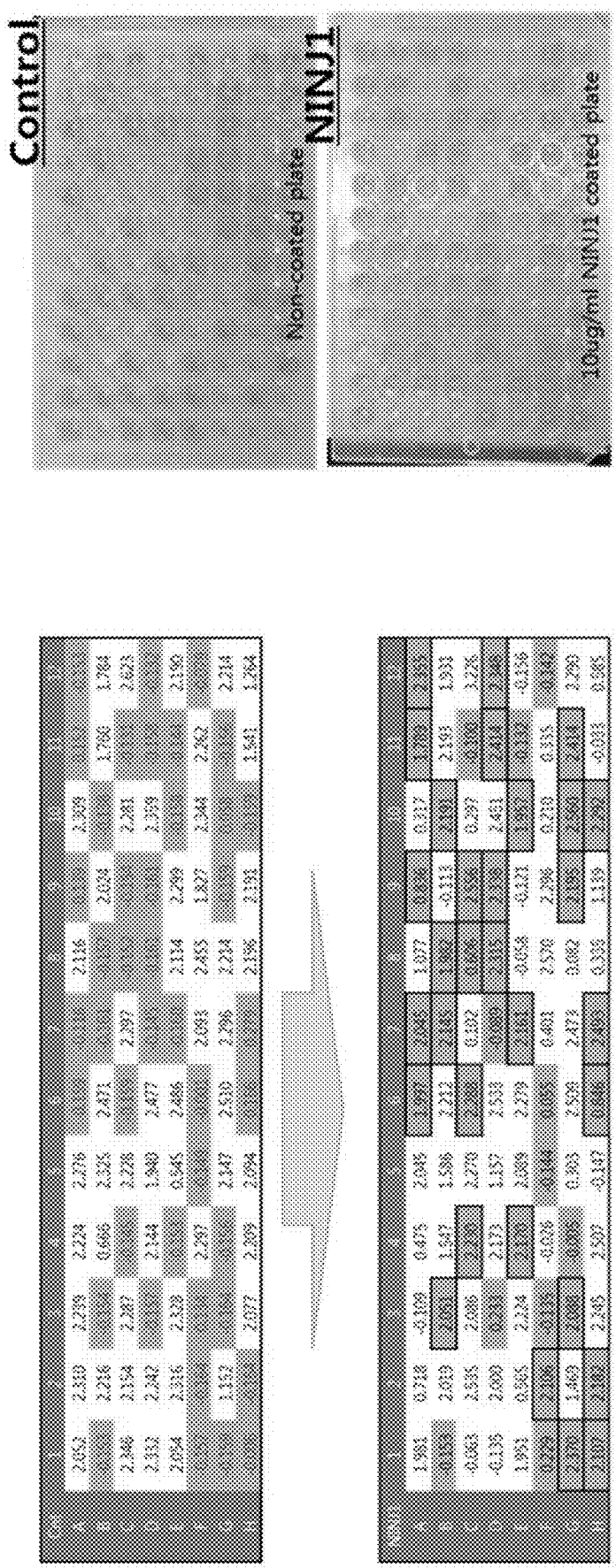
FIG. 2 shows the results of confirming and screening the affinity of HBAg1 (P26-N37 region) through ELISA, for the phage candidates selected through the 3rd round bio-panning process.

When the results of the control and HBAg1-coated plates were compared, as shown in FIG. 2, DNA sequence analysis of colonies of the wells in which the reaction was observed only in HBAg1 was performed. This resulted in a number of scFv candidates (indicated by green in FIG. 2) that could specifically bind to human NINJ-1, particularly HBAg1.

EXAMPLE 2

Expression and Purification of Recombinant Proteins of NINJ-1

2-1. Preparation of Expression Vector for the Production of the Extracellular Domain Protein of NINJ-1

Figure 3A:
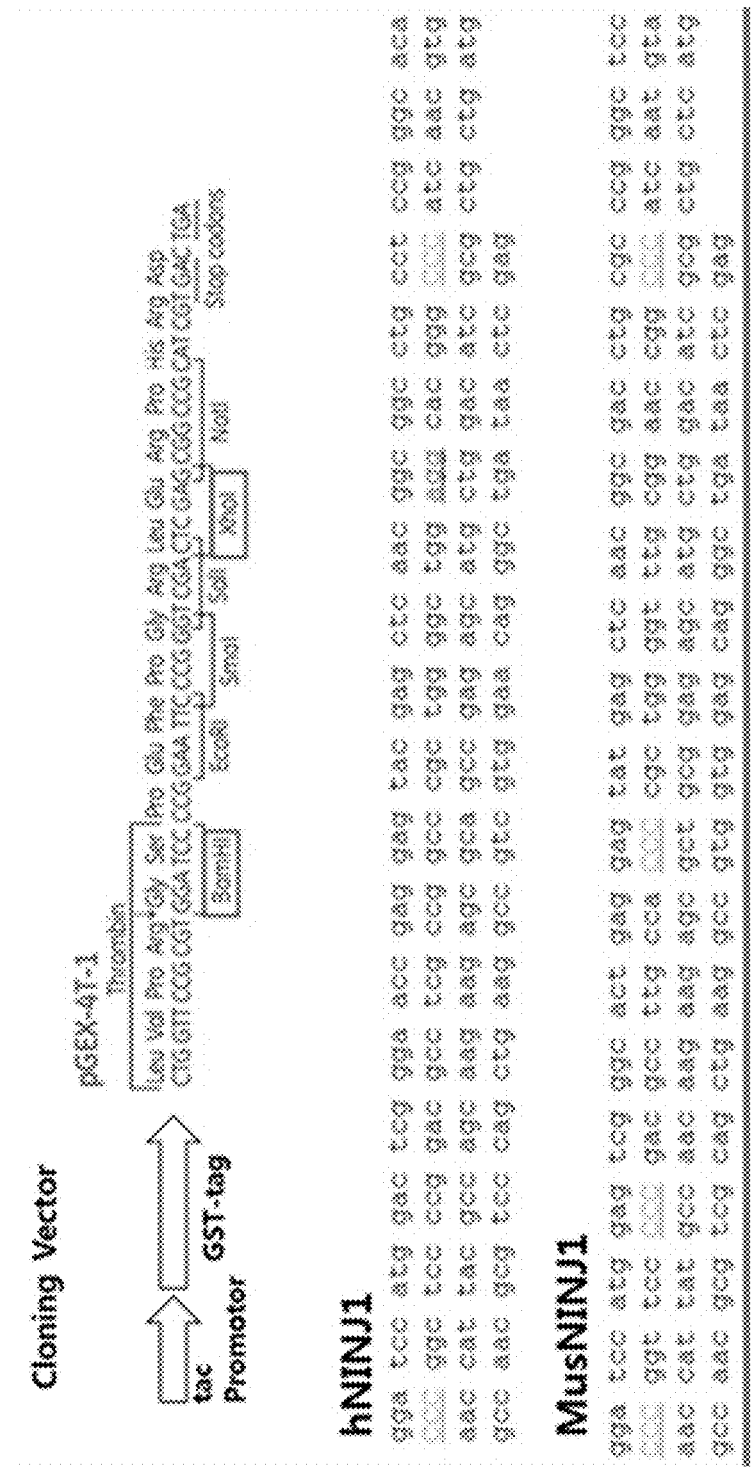
FIG. 3A shows the human NINJ-1 extracellular domain nucleic acid sequence and mouse NINJ-1 extracellular domain nucleic acid sequence introduced into the pGEX-4T-1 expression vector. From top to bottom: SEQ ID NOS: 33-37.
Figure 3B:
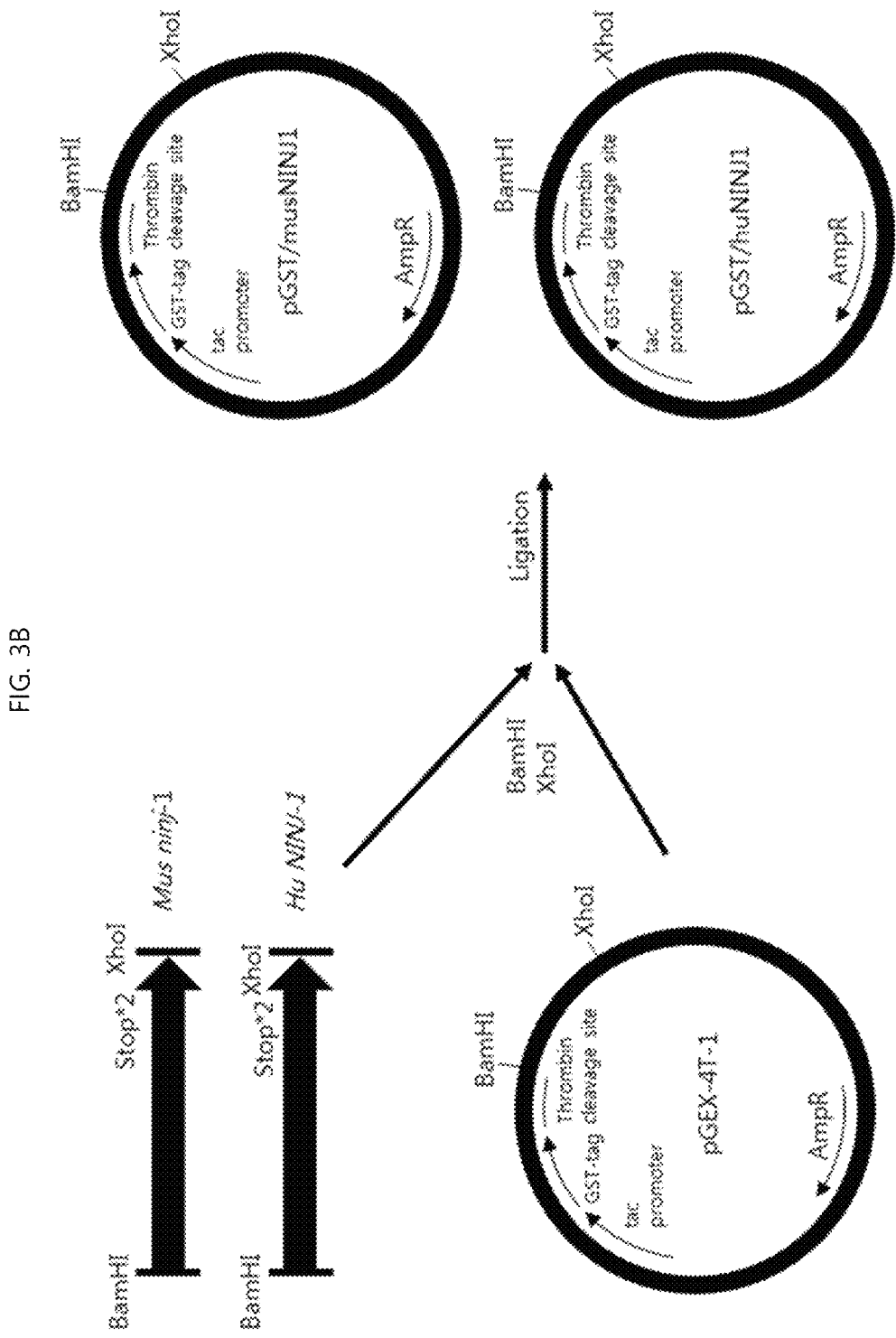
FIG. 3B is a schematic diagram showing a cleavage site of a vector for the introduction of a human NINJ-1 extracellular domain nucleic acid sequence or a mouse NINJ-1 extracellular domain nucleic acid sequence, and a finally prepared expression vector.

In order to confirm whether the scFv candidates obtained in Example 1 can structurally bind to the P26-N37 region of the human NINJ-1 protein and can bind to the extracellular domain portion of NINJ-1, a nucleotide sequence containing two transcription termination codons in the extracellular domain portion of the human NINJ-1 or mouse NINJ-1 gene was inserted between the multi-cloning sites BamHI and XhoI in the pGEX-4T-1 expression vector to construct a recombinant protein expression vector, respectively. The specific nucleotide sequence is shown in FIG. 3A, and each specific cloning region is shown in FIG. 3B, and each expression vector was named pGST/huNINJ1 and pGST/musNINJ1, respectively. The expression vectors were transfected into *E. coli* DH5a (enzynomics) and cultured. After the MIDI prep, the insertion of GST/huNINJ-1 and GST/musNINJ-1 was finally confirmed through DNA sequencing.

2-2. Expression and Purification of NINJ-1 Extracellular Domain Protein

Figure 4:
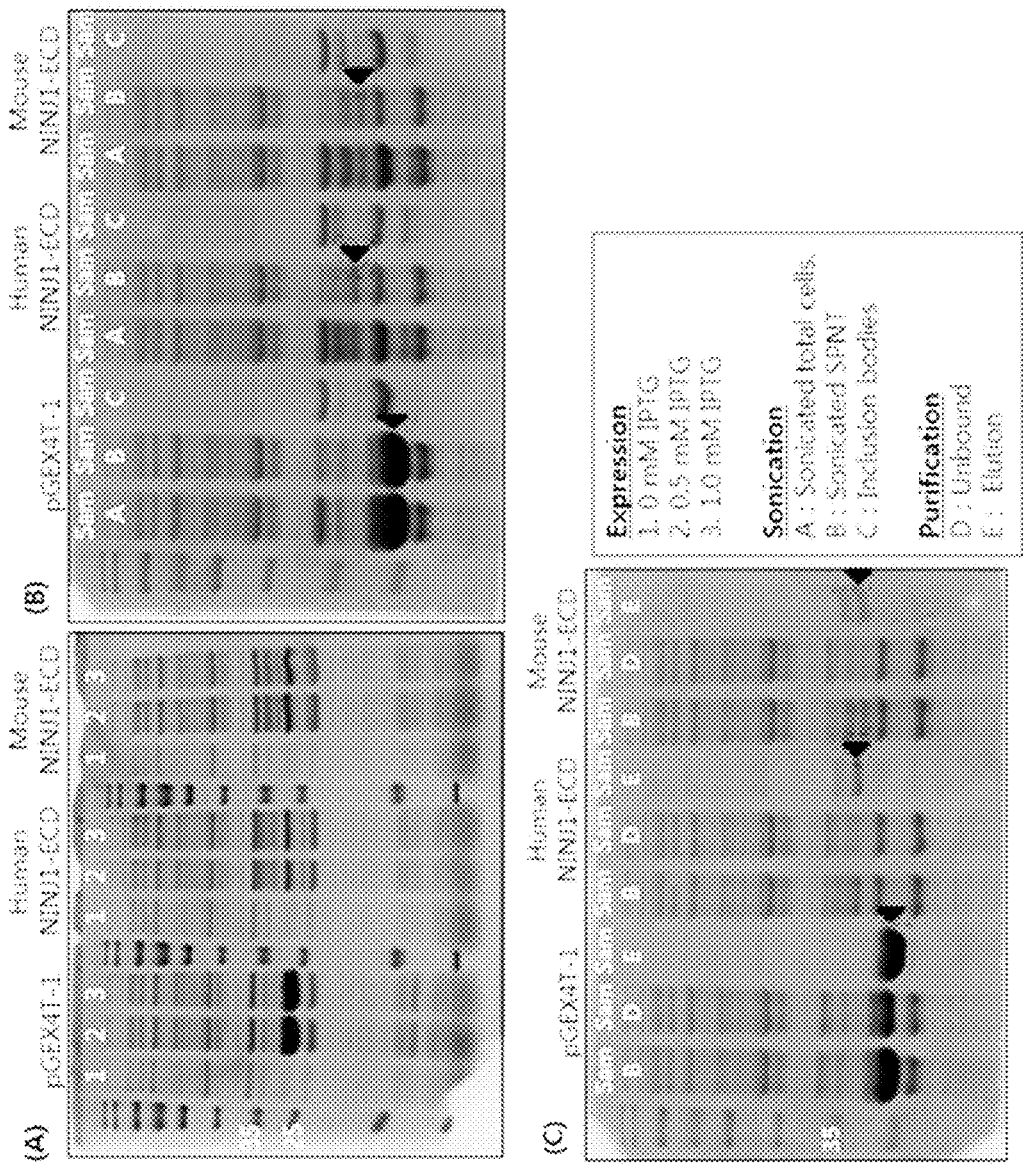
FIG. 4 shows the results of SDS-PAGE analysis of GST/huNINJ-1 protein expression and GST/musNINJ-1 protein expression in the transformed E. coli (FIG. 4A: expression, FIG. 4B: Sonication, FIG. 4C: Purification).

*E. coli* DH5a transformed with the expression vector pGST/huNINJ-1 or pGST/musNINJ-1 prepared in Example 2-1 was subjected to MIDI prep. After sufficient plasmid DNA was recovered, the following experiment was performed for the expression and purification of recombinant proteins in *E. coli*. *E. coli* BL21DE3 was transformed with pGST/huNINJ-1 or pGST/musNINJ1 plasmid DNA, respectively, and cultured in LB medium. Then, a single colony was cultured in a 5 ml LB liquid medium containing ampicillin so that the OD 600 value was 0.6 to 0.8. Then, the medium was treated with 0 mM, 0.5 mM, and 1 mM of IPTG, respectively, cultured at 37° C. for 3 hours, and centrifuged at 8,000 rpm for 10 minutes to recover only cells. SDS-PAGE was performed on the cell lysate, and expression was confirmed by treating with Coomassie stain (Sigma Aldrich) (FIG. 4A).

The cell lysate, which had been induced to express with 0.5 mM and 1.0 mM IPTG, was collected and centrifuged to recover cells. Cells were homogenized with 1 ml PBS and were lysed using an ultrasonicator (BRANSON). Then, the dissolved cells were centrifuged to separate inclusion bodies and water-soluble proteins, and the separated samples were subjected to SDS-PAGE and Coomassie stain treatment to confirm the water-solubility of the recombinant proteins (FIG. 4B). Then, the water-soluble protein portion was reacted with Glutathione Sepharose™ 4B resin (GE healthcare Life Sciences) for 1 hour at 4° C., centrifuged to separate the protein bound to the resin. Then, only the GST-tagged recombinant protein was recovered using 50 mM Tris-HCl, 10 mM reduced glutathione and pH 8.0 buffer. SDS-PAGE was performed on the recovered protein, and purification was performed by the same method using a coomassie stain to confirm the size of the recovered protein (FIG. 4C).

EXAMPLE 3

Affinity Measurement of GST/huNINJ-1 and GST/musNINJ-1 by ELISA

In order to screen scFv candidates capable of specifically binding to the recombinant proteins GST/huNINJ-1 and GST/musNINJ-1 obtained in Example 2, the following experiment was performed. Experiments were performed to confirm the affinity of scFv candidate groups that specifically showed binding activity to HBAg1 in Example 1 and GST/huNINJ-1 and GST/musNINJ-1, using B1 in which no specific binding to HBAg1 was observed as a control. Recombinant proteins GST/huNINJ-1, GST/musNINJ-1 or GST were coated at a concentration of 10 ug/ml in a 96 well plate (corning 3690 flat bottom, half-area plate), respectively. The scFv phage particles in the cells were separated from the scFv candidate group selected in Example 1 through the same experimental method as in Example 1-2. Then, ELISA was performed using the coated plates.

The absorbance values at 430 nm indicated by each candidate group were normalized to the values of B1 (Non-binding active control), and finally, four candidates (D9, D12, E4 and G11) with high affinity to GST/HuNINJ-1 and GST/musNINJ-1 were selected among candidates showing affinity to HBAg1. As shown in FIG. 5, the affinities of human and mouse NINJ-1 were confirmed in four candidate groups, and CDR sequences of these candidate groups are shown in Table 1 below.

TABLE 1

|   | CDRH1 | CDRH2 | CDRH3 | CDRL1 | CDRL2 | CDRL3 |
|---|---|---|---|---|---|---|
| D9 | DYSMS | GIYPDDSNTY YADSVKG | DPVHCERSV CYYADAMDV | RGSSSNI GSNYVT | ADSHR PS | GAWDS SLNA |
| D12 | NYDMS | WISPDGSNIY YADSVKG | YRITPMSWL SYYDDAMDV | TGSSSNI GSNSVT | SDSKR PS | GSWDY SLNA |
| E4 | DYAMS | GIYHGGGNT YYADSVKG | DPMHSERIT FDY | SGSSSNI GSNNVS | DNSKR PS | GTWDY SLSA |
| G11 | DYAMS | AIYYDSGSIY ADSVKG | DPMTSLALT FDY | SGSSSNI GSNYVS | DNSQR PS | GAWDA SLNG |

EXAMPLE 4

Preparation of Expression Vector for Human Anti-NINJ-1 Antibody Production and Antibody Production In order to express the immunoglobulin G (IgG) antibody having a molecular weight of 160 kDa containing the VH and VL nucleotide sequences of the selected four scFvs (D9, D12, E4 and G11), the following cloning was performed.

As shown in FIG. 6, VH and VL nucleotide sequences of each scFv were inserted into IgG expression vectors (Modified pOptiVEC (IgG VL-LC$_K$ notation, light chain constant region comprised; Thermo Fisher Scientific, pOptiVEC-TOPO TA cloning kit, Cat No. 12744-017), Modified pcDNA3.3 TOPO (IgG VH-HC notation, heavy chain constant region comprised; Thermo Fisher Scientific, pcDNA3.3-TOPO TA cloning kit, Cat No. K830001) ClaI and NheI regions using the primers shown in Table 2 below to prepare heavy chain expression vectors (IgG VH-HC) and light chain expression vectors (IgG VL-LC$_K$) (See FIG. 6). Then, the vectors were transformed into E. coli; cultured on a liquid medium, and plasmid DNA was extracted through a midi prep. The extracted plasmid DNA was co-transfected into the FreeStyle 293F cell line according to the experimental method provided in Freestyle 293 Expression system (Thermo Fisher Scientific) to induce the expression of the immunoglobulin G type antibody. The cell culture was centrifuged to separate the cells, and then the antibodies were separated and purified by affinity chromatography using MabSelect SuRe™ Protein A (GE Healthcare Life Sciences).

TABLE 2

Information of primers

| Primer | Sequence | SEQ ID NO. |
|---|---|---|
| IgG-VH-HC forward primer | ATTCGATCGATATGGAGACAGACACACTCCTGCTA TGGGTACTGCTGCTCTGGGTTCCAGGTTCCACGTG GGAGGTGCAGCTGTTGGAGTCT | 28 |
| IgG-VH-HC reverse primer | CTTGGTGCTAGCTGAGCTCACGGTGACCAGTGT ATTCGATCGATATGGAGACAGACACACTCCTGCTA | 29 |
| IgG-VL-LC forward primer | TGGGTACTGCTGCTCTGGGTTCCAGGTTCCACGTG GCAGTCTGTGCTGACTCAGCCA | 30 |
| IgG-VL-LC reverse primer | AGCCACCGTACGTAGGACCGTCAGCTTGGTGCC | 31 |

EXAMPLE 5

Affinity Measurement of Human Anti-NINJ-1 IgG Against HBAg1

D12 was used as a representative Ig antibody prepared in Example 4, and affinity to the P26-N37 region was measured using NINJ-1 antibodies (MAB51051, BD610776, SC-136295) that are commercially available from other companies as a control.

Specifically, HBAg1 was coated on 96-well plates (Thermo scientific, Cat No. 436014) coated with streptavidin at a concentration of 10 ug/ml overnight at 4° C. After washing three times with TBS buffer containing 0.05% Tween 20, 3% bovine serum albumin (BSA) was dissolved again in the same buffer, and then reacted at room temperature for 1 hour. Various anti-NINJ-1 antibodies that are commercially available from other companies and the Ig antibodies of the present invention were diluted 2-fold at a concentration of 5 ug/ml or 25 ug/ml, reacted at room temperature for 1 hour in each well, and then a secondary antibody conjugated with horseradish peroxidase was added and reacted for 1 hour. After reacting with TMB for 20 minutes, the reaction was stopped with 1N $H_2SO_4$ and the absorbance was measured at 430 nm.

As a result, as shown in FIGS. 7A and 7B, it was confirmed that the D12 Ig antibody of the present invention was found to have a significantly higher affinity for the human P26-N37 peptide than the anti-NINJ-1 antibody that are commercially available from other companies.

EXAMPLE 6

Normal Cell-Based Anti-NINJ-1 IgG Screening

It was confirmed whether the four candidate groups selected above and the experimental groups belonging to the candidate group of Example 1-2 but excluded later were specifically bound to the NINJ-1 protein expressed in actual human cell lines. Also, it was confirmed by using a flow cytometer whether the antigen recognition sites of the anti-NINJ-1 antibodies that are commercially available from other companies are the same.

Human cerebral microvascular endothelial cell line (hCMEC/D3) were treated with 10% fetal bovine serum (Hyclone) for 20 minutes at 4° C., and then mouse-derived anti-NINJ-1 antibody (R&D systems, MAB51051), Isotype control (R&D systems, MAB002), and the selected human anti-NINJ-1 antibody (D9, D12, E4, G11 and 8 additional antibodies, all tested in Ig form) were reacted at 4° C. for 90 minutes at a concentration of 1 ug per 10,000 cells. After completion of the reaction, the cells were washed three times with PBS, and then the mouse-derived antibody was reacted with anti-mouse IgG with a secondary antibody conjugated with FITC, Human-derived antibodies (antibodies of the invention) were reacted with anti-human IgG secondary antibody conjugated with FITC for 1 hour at 4° C. This assay was performed using flow cytometry (BD FACS Calibur™)

As shown in FIG. 8A, it was shown that the four antibodies of the present invention specifically bind to human NINJ-1 expressing in the cells, while D9, D12, and G11 among the four selected antibodies showed particularly high binding ability.

In addition, using the D12 of the candidate groups, it was confirmed whether or not it shares the antigen recognition site with the anti-NINJ-1 antibody (R&D systems) commercially available from other companies. Each of the antibodies was treated at the same concentration of 1 ug per 10,000 cells in the immortalized-Human cerebral microvascular endothelial cell line (HBMEC), and then, the anti-human IgG secondary antibody conjugated with FITC was reacted at 4° C. for 1 hour. This assay confirmed binding using a flow cytometer (BD FACS Calibur™). As shown in FIG. 8B, it was confirmed that the antibody D12 of the present invention does not share the antigen recognition sites with the anti-NINJ-1 antibody (R&D systems) commercially available from other companies.

EXAMPLE 7

Confirmation of Diagnostic Specificity for NINJ-1

In the treatment of doxycycline, the specific binding ability of the four candidate groups (D9, D12, E4, G11) tested through Example 3 and Example 4 to human NINJ-1 protein was verified using a glioblastoma cell line overexpressing NINJ-1.

7-1. Construction of Expression Vector and Stable Expression Cells for Doxycycline-Inducible Human NINJ-1 Over-Expressing Cell Lines In order to construct a human NINJ-1 over-expressing cell line, the cloning positions in the cDNA sequence of NINJ-1 (Korea Human Gene Bank, hMU007113) were selected from CDS 21 to 476 (ATGGACTC to AGCAGTAG), and cloning primers were prepared using BamHI and EcoRI in the MCS portion of the pLVX-Tet-On puro vector.

PCR (95° C./5 min, (95° C./30 sec, 60° C./45 sec, 72° C./30 sec) 30 times, 72° C./10 min) was performed using a forward primer 5'-TATGGATCCCTACTGCTGGGGTGC-CATG-3' (SEQ ID NO:32) and a reverse primer 5'-TAT-GAATTCATGGACTCGGGAACCGAGG-3' (SEQ ID NO:33), and then electrophoresis on 0.7% agarose gel to recover only specific fragments, and the vector and PCR products were reacted with BamHI and EcoRI for 1 hour at 37° C. After completion of the reaction, the sample was recovered and purified, and the inducible expression vector was completed through T4 ligase (This process is shown in FIG. 9A). The inducible expression vector was transfected into a glioblastoma cell line (U87MG), and puromycin was repeatedly treated at a concentration of 1 ug/ml for 3 days to establish a stable cell line. 1, 5, 10, and 50 ng/ml of doxycycline was added to the growth medium of the stable cells, and the increase of the expression rate of NINJ-1 was confirmed by Western blotting (see FIG. 9B). It was shown that the expression level of NINJ1 protein increased according to the concentration of doxycyclin (see FIG. 9B). These cell lines are hereinafter referred to as U87MG pLVX NINJ1.

7-2. Measurement of Binding Capacity Based on Doxycycline-Inducible Human NINJ-1 Over-Expressing Cell Lines In order to compare the binding ability with the human anti-NINJ-1 IgG candidate group finally selected in Example 4 (D9, D12, E4, G11) and the anti-NINJ-1 antibody developed and marketed by another company (BD bioscience, SantaCruz), the following experiment was performed using a glioblastoma cell line (U87MG pLVX NINJ1) in which human NINJ-1 overexpression was induced by the doxycycline prepared in Example 7-1.

In advance, a cell line was prepared by treatment of the U87MG pLVX NINJ-1 glioblastoma cell line with a final concentration of 50 ng/ml for 24 hours at 37° C. Based on F4 (control), which was excluded from Example 3, the four candidates of the present invention and two anti-NINJ-1 antibodies of other companies (BD bioscience, SantaCruz) were analyzed, using a flow cytometry analyzer according to the same experimental method as in Example 6.

As shown in FIG. 10, it was confirmed that the 4-candidate groups possess the high binding ability to NINJ-1 as compared with the antibody marketed by other companies (FIGS. 10A and 10B).

EXAMPLE 8

Inhibition of Adhesion of Cerebral Vascular Endothelial Cells and Immune Cells after Treatment with Anti-NINJ-1 IgG of the Present Invention Binding of immune cells to central nervous system endothelial cells and migration of immune cells into the central nervous system are important pathology in multiple sclerosis, and existing therapeutic strategies (for example natalizumab, etc.) for preventing such binding and migration have been used in the treatment of multiple sclerosis. It is known in the art that NINJ-1 acts as an adhesion molecule in the binding of immune cells to central nervous system endothelial cells and migration of the immune cells into the central nervous system. Therefore, if the activity of NINJ-1 is inhibited and binding of immune cells to central nervous system endothelial cells and migration of the immune cells is thus inhibited, the prevention and treatment of multiple sclerosis can be achieved.

In order to confirm whether the human NINJ-1 Ig antibody prepared by the present invention can inhibit adhesion between the immune cell line and human cerebral endothelial cells, the following experiment was conducted.

Collagen I Rat tail Protein was coated at a concentration of 50 ug/ml in a 96-well plate, and $1.0 \times 10^4$ hCMEC/D3 cell lines were cultured in each well at 37° C. and 5% $CO_2$ for 72 hours. Then, 200 IU/ml TNFα and IFNγ or 1 μg/ml PMA were treated for 16 hours. Then, the cells were washed twice with magnesium and calcium-free DPBS to remove inflammation inducers remaining in the cells. Thereafter, 10 ug/ml of each antibody was added to the wells and reacted. At the end of this procedure, the remaining antibody was removed by washing twice with DPBS again. Then, $1.0 \times 10^4$ U937 cell lines (lymphoblast) expressing Green fluorescent protein (GFP) as immune cells were added, and the cells were washed three times with DPBS after inducing adhesion at 37° C. and 5% $CO_2$ for 90 minutes. All procedures were performed using a real-time cell image analyzer (IncuCyte™ ZOOM) to measure the number of green-labeled cells. The number of cells finally remaining in each well was divided by the initial cell number, and then standardized based on the treatment with PMA (Sigma Aldrich).

As shown in FIG. 11, adhesion between the immune cell line and human cerebral endothelial cells was decreased in the group treated with human NINJ-1 antibody (1 μg/ml PMA+D12, 1 μg/ml PMA+G11). Thus, it was confirmed that the antibodies prepared by the present invention inhibit the adhesion between the immune cells and the human cerebral endothelial cells through their specific binding ability to the P26-N37 region. Thus, it is apparent that the antibodies prepared in the present invention can exhibit a therapeutic effect on multiple sclerosis.

INDUSTRIAL APPLICABILITY

As described above, the present invention provides an antibody or antigen-binding fragment thereof that specifically binds to a human NINJ-1 and the homologous binding site of the protein. The antibody or antigen-binding fragment thereof according to the present invention has a very high binding affinity and specificity to human NINJ-1 and does not show cross-reactivity with other origin-derived NINJ-1 proteins (especially mouse NINJ-1 protein) having high protein similarity. Thus, it provides significant advantages not only in the diagnosis of diseases related to NINJ-1 protein, but also in the accuracy, high sensitivity and the like in inhibiting the pathological conditions involved in NINJ-1 protein. In particular, the antibody provided by the present invention is remarkably effective in inhibiting adhesion between immune cells and human cerebral endothelial cells, and thus has therapeutic effect on multiple sclerosis. Therefore, the present invention is highly industrially applicable in the diagnostic and therapeutic industries where targeting characteristics are important.

What is claimed is:

1. An antibody or antigen-binding fragment thereof that specifically binds to a residue region between 26th and 37th in a human-derived Ninjurin-1 (NINJ-1) protein sequence defined by SEQ ID NO: 25, wherein the antibody or antigen-binding fragment thereof comprises:
    an antibody light chain variable region (VL) comprising a complementarity determining region (CDR) L1 comprising the amino acid sequence defined by SEQ ID NO: 7, a complementarity determining region (CDR) L2 comprising the amino acid sequence defined by SEQ ID NO: 8, and a complementarity determining region (CDR) L3 comprising the amino acid sequence defined by SEP ID NO: 9; and
    an antibody heavy chain variable region (VH) comprising a complementarity determining region (CDR) H1 comprising the amino acid sequence defined by SEQ ID NO: 10, a complementary determining region (CDR) H2 comprising the amino acid sequence defined by SEQ ID NO: 11, and a complementarity determining region (CDR) H3 comprising the amino acid sequence defined by SEP ID NO: 12.

2. The antibody or antigen-binding fragment thereof of claim 1, wherein the antigen-binding fragment is selected from the group consisting of diabody, Fab, Fab', F(ab)2, F(ab') 2, Fv and scFv of the antibody.

3. A composition comprising the antibody or antigen-binding fragment thereof of claim 1 as an active ingredient.

4. An isolated polynucleotide molecule comprising a polynucleotide encoding the antibody or antigen-binding fragment thereof of claim 1.

5. A vector comprising the polynucleotide molecule of claim 4.

6. An isolated host cell comprising the vector of claim 5.

7. A method for preparing an antibody or an antigen-binding fragment thereof that specifically binds to a human NINJ-1 protein defined by the amino acid sequence of SEQ ID NO: 25, the method comprising the steps of:
    culturing the host cell of claim 6 in a medium to express and produce the antibody or antigen-binding fragment thereof; and recovering the antibody or antigen-binding fragment thereof from the host cell or the medium in which the host cell has been cultured, wherein the antibody or antigen-binding fragment thereof comprises the VL comprising the CDRL1-3 of SEQ ID NOs: 7-9 respectively and the VH comprising the CDR1-3 of SEQ ID NOs: 10-12 respectively.

8. A method of specifically detecting human NINJ-1, the method comprising the steps of:
    contacting the antibody or antigen-binding fragment thereof of claim 1 with a biological sample expressing or comprising human NINJ-1 defined by the amino acid sequence of SEQ ID NO: 25; and
    detecting the presence of the complex of the antibody or antigen-binding fragment thereof binding to the human NINJ-1;
    wherein the biological sample is a tissue or cell or is isolated from a tissue or cell.

* * * * *

SEQUENCE LISTING

```
<160> NUMBER OF SEQ ID NOS: 37

<210> SEQ ID NO 1
<211> LENGTH: 13
<212> TYPE: PRT
<213> ORGANISM: Artificial Sequence
<220> FEATURE:
<223> OTHER INFORMATION: VL-CDR1 of NINJ1 D9

<400> SEQUENCE: 1

Arg Gly Ser Ser Ser Asn Ile Gly Ser Asn Tyr Val Thr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: VL-CDR2 of NINJ1 D9

<400> SEQUENCE: 2

Ala Asp Ser His Arg Pro Ser
1               5

<210> SEQ ID NO 3
<211> LENGTH: 9
```

```
<212> TYPE: PRT
<213> ORGANISM: Artificial Sequence
<220> FEATURE:
<223> OTHER INFORMATION: VL-CDR3 of NINJ1 D9

<400> SEQUENCE: 3

Gly Ala Trp Asp Ser Ser Leu Asn Ala
1               5

<210> SEQ ID NO 4
<211> LENGTH: 5
<212> TYPE: PRT
<213> ORGANISM: Artificial Sequence
<220> FEATURE:
<223> OTHER INFORMATION: VH-CDR1 of NINJ1 D9

<400> SEQUENCE: 4

Asp Tyr Ser Met Ser
1               5

<210> SEQ ID NO 5
<211> LENGTH: 17
<212> TYPE: PRT
<213> ORGANISM: Artificial Sequence
<220> FEATURE:
<223> OTHER INFORMATION: VH-CDR2 of NINJ1 D9

<400> SEQUENCE: 5

Gly Ile Tyr Pro Asp Asp Ser Asn Thr Tyr Tyr Ala Asp Ser Val Lys
1               5                   10                  15

Gly

<210> SEQ ID NO 6
<211> LENGTH: 18
<212> TYPE: PRT
<213> ORGANISM: Artificial Sequence
<220> FEATURE:
<223> OTHER INFORMATION: VH-CDR3 of NINJ1 D9

<400> SEQUENCE: 6

Asp Pro Val His Cys Glu Arg Ser Val Cys Tyr Tyr Ala Asp Ala Met
1               5                   10                  15

Asp Val

<210> SEQ ID NO 7
<211> LENGTH: 13
<212> TYPE: PRT
<213> ORGANISM: Artificial Sequence
<220> FEATURE:
<223> OTHER INFORMATION: VL-CDR1 of NINJ1 D12

<400> SEQUENCE: 7

Thr Gly Ser Ser Ser Asn Ile Gly Ser Asn Ser Val Thr
1               5                   10

<210> SEQ ID NO 8
<211> LENGTH: 7
<212> TYPE: PRT
<213> ORGANISM: Artificial Sequence
<220> FEATURE:
<223> OTHER INFORMATION: VL-CDR2 of NINJ1 D12

<400> SEQUENCE: 8

Ser Asp Ser Lys Arg Pro Ser
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: VL-CDR3 of NINJ1 D12

<400> SEQUENCE: 9

Gly Ser Trp Asp Tyr Ser Leu Asn Ala
1               5

<210> SEQ ID NO 10
<211> LENGTH: 5
<212> TYPE: PRT
<213> ORGANISM: Artificial Sequence
<220> FEATURE:
<223> OTHER INFORMATION: VH-CDR1 of NINJ1 D12

<400> SEQUENCE: 10

Asn Tyr Asp Met Ser
1               5

<210> SEQ ID NO 11
<211> LENGTH: 17
<212> TYPE: PRT
<213> ORGANISM: Artificial Sequence
<220> FEATURE:
<223> OTHER INFORMATION: VH-CDR2 of NINJ1 D12

<400> SEQUENCE: 11

Trp Ile Ser Pro Asp Gly Ser Asn Ile Tyr Tyr Ala Asp Ser Val Lys
1               5                   10                  15

Gly

<210> SEQ ID NO 12
<211> LENGTH: 18
<212> TYPE: PRT
<213> ORGANISM: Artificial Sequence
<220> FEATURE:
<223> OTHER INFORMATION: VH-CDR3 of NINJ1 D12

<400> SEQUENCE: 12

Tyr Arg Ile Thr Pro Met Ser Trp Leu Ser Tyr Tyr Asp Asp Ala Met
1               5                   10                  15

Asp Val

<210> SEQ ID NO 13
<211> LENGTH: 13
<212> TYPE: PRT
<213> ORGANISM: Artificial Sequence
<220> FEATURE:
<223> OTHER INFORMATION: VL-CDR1 of NINJ1 E4

<400> SEQUENCE: 13

Ser Gly Ser Ser Ser Asn Ile Gly Ser Asn Asn Val Ser
1               5                   10

<210> SEQ ID NO 14
<211> LENGTH: 7
<212> TYPE: PRT
<213> ORGANISM: Artificial Sequence
<220> FEATURE:
<223> OTHER INFORMATION: VL-CDR2 of NINJ1 E4

<400> SEQUENCE: 14
```

```
Asp Asn Ser Lys Arg Pro Ser
1               5

<210> SEQ ID NO 15
<211> LENGTH: 9
<212> TYPE: PRT
<213> ORGANISM: Artificial Sequence
<220> FEATURE:
<223> OTHER INFORMATION: VL-CDR3 of NINJ1 E4

<400> SEQUENCE: 15

Gly Thr Trp Asp Tyr Ser Leu Ser Ala
1               5

<210> SEQ ID NO 16
<211> LENGTH: 5
<212> TYPE: PRT
<213> ORGANISM: Artificial Sequence
<220> FEATURE:
<223> OTHER INFORMATION: VH-CDR1 of NINJ1 E4

<400> SEQUENCE: 16

Asp Tyr Ala Met Ser
1               5

<210> SEQ ID NO 17
<211> LENGTH: 17
<212> TYPE: PRT
<213> ORGANISM: Artificial Sequence
<220> FEATURE:
<223> OTHER INFORMATION: VH-CDR2 of NINJ1 E4

<400> SEQUENCE: 17

Gly Ile Tyr His Gly Gly Gly Asn Thr Tyr Tyr Ala Asp Ser Val Lys
1               5                   10                  15

Gly

<210> SEQ ID NO 18
<211> LENGTH: 12
<212> TYPE: PRT
<213> ORGANISM: Artificial Sequence
<220> FEATURE:
<223> OTHER INFORMATION: VH-CDR3 of NINJ1 E4

<400> SEQUENCE: 18

Asp Pro Met His Ser Glu Arg Ile Thr Phe Asp Tyr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: VL-CDR1 of NINJ1 G11

<400> SEQUENCE: 19

Ser Gly Ser Ser Ser Asn Ile Gly Ser Asn Tyr Val Ser
1               5                   10

<210> SEQ ID NO 20
<211> LENGTH: 7
<212> TYPE: PRT
<213> ORGANISM: Artificial Sequence
<220> FEATURE:
<223> OTHER INFORMATION: VL-CDR2 of NINJ1 G11

<400> SEQUENCE: 20
```

```
Asp Asn Ser Gln Arg Pro Ser
1               5

<210> SEQ ID NO 21
<211> LENGTH: 9
<212> TYPE: PRT
<213> ORGANISM: Artificial Sequence
<220> FEATURE:
<223> OTHER INFORMATION: VL-CDR3 of NINJ1 G11

<400> SEQUENCE: 21

Gly Ala Trp Asp Ala Ser Leu Asn Gly
1               5

<210> SEQ ID NO 22
<211> LENGTH: 5
<212> TYPE: PRT
<213> ORGANISM: Artificial Sequence
<220> FEATURE:
<223> OTHER INFORMATION: VH-CDR1 of NINJ1 G11

<400> SEQUENCE: 22

Asp Tyr Ala Met Ser
1               5

<210> SEQ ID NO 23
<211> LENGTH: 17
<212> TYPE: PRT
<213> ORGANISM: Artificial Sequence
<220> FEATURE:
<223> OTHER INFORMATION: VH-CDR2 of NINJ1 G11

<400> SEQUENCE: 23

Ala Ile Tyr Tyr Asp Ser Gly Ser Ile Tyr Tyr Ala Asp Ser Val Lys
1               5                   10                  15

Gly

<210> SEQ ID NO 24
<211> LENGTH: 12
<212> TYPE: PRT
<213> ORGANISM: Artificial Sequence
<220> FEATURE:
<223> OTHER INFORMATION: VH-CDR3 of NINJ1 G11

<400> SEQUENCE: 24

Asp Pro Met Thr Ser Leu Ala Leu Thr Phe Asp Tyr
1               5                   10

<210> SEQ ID NO 25
<211> LENGTH: 152
<212> TYPE: PRT
<213> ORGANISM: Artificial Sequence
<220> FEATURE:
<223> OTHER INFORMATION: human Ninjurin 1 protein

<400> SEQUENCE: 25

Met Asp Ser Gly Thr Glu Glu Tyr Glu Leu Asn Gly Gly Leu Pro Pro
1               5                   10                  15

Gly Thr Pro Gly Ser Pro Asp Ala Ser Pro Ala Arg Trp Gly Trp Arg
                20                  25                  30

His Ser Pro Ile Asn Val Asn His Tyr Ala Ser Lys Lys Ser Ala Ala
            35                  40                  45

Glu Ser Met Leu Asp Ile Ala Leu Leu Met Ala Asn Ala Ser Gln Leu
        50                  55                  60
```

```
Lys Ala Val Val Glu Gln Gly Pro Ser Phe Ala Phe Tyr Val Pro Leu
 65                  70                  75                  80

Val Val Leu Ile Ser Ile Ser Leu Val Leu Gln Ile Gly Val Gly Val
                 85                  90                  95

Leu Leu Ile Phe Leu Val Lys Tyr Asp Leu Asn Asn Pro Ala Lys His
            100                 105                 110

Ala Lys Leu Asp Phe Leu Asn Asn Leu Ala Thr Gly Leu Val Phe Ile
        115                 120                 125

Ile Val Val Val Asn Ile Phe Ile Thr Ala Phe Gly Val Gln Lys Pro
130                 135                 140

Leu Met Asp Met Ala Pro Gln Gln
145                 150

<210> SEQ ID NO 26
<211> LENGTH: 1297
<212> TYPE: DNA
<213> ORGANISM: Artificial Sequence
<220> FEATURE:
<223> OTHER INFORMATION: Homo sapiens ninjurin 1 (NINJ1)

<400> SEQUENCE: 26
cgcagctgga gcctgcggct gaggctcggg cgcgctcagg cccggatcct ggcggcctgg      60
gcggccgcac catggactcg gaaccgagg agtacgagct caacggcggc ctgcctccgg     120
gcacacccgg ctccccggac gcctcgccgg cccgctgggg ctggaggcac gggcccatca     180
acgtgaacca ttacgccagc aagaagagcg cagccgagag catgctggac atcgcgctgc     240
tgatggccaa cgcgtcccag ctgaaggccg tcgtggaaca gggccccagc ttcgccttct     300
atgtgcccct ggtggtcctc atctccatct cccttgtgct gcagatcggc gtgggggtgc     360
tgctcatctt ccttgtcaag tacgacctta caacccggc caagcacgcc aagctggact     420
tcctcaacaa cctggccacg ggcctggtgt tcatcatcgt ggtagtcaac atcttcatca     480
cggccttcgg ggtccagaag cccttgatgg acatggcacc ccagcagtag gacacccagg     540
accctggatg ctgcctgccc tgcaactcag ctgcccgacc caggagtcg ccatacctgt     600 gaggtgtcca cctccctgca catggcacta cccagactgc cagagcccag gctggcctca     660
tctgcaccat gtccccggac cagcccttgc tctgactgcg ccaagcacc acgcaggagg     720 ccactcttgt ctctcagcag ctgttcccag gaggcagctc cctcctggca catgggggct     780
ggccacaata gcccagaggg tcagaactgg acagctgcag agacctgtgc cagagaagg     840 gtctcgaccc actcaaggac acacagcagg tccgtggatg ggctggatga gtgaccaggg     900
ccagcctctg tctcaggaca ttccagaagg acaaggagat gtctctccct ctcccaaagc     960
accagcgtcc ctgcctcccg tgggccctgt ccgggttgcc ctggtgaccc cagcctctgt    1020
ccacttccta acccagggac cctgcacagc cagaactgcc tttggcccta cggatggcca    1080
ctggctctgg tcttaagtgc ctgggcttgg tggccatcaa gagggagcca gtcaggcctg    1140
tgagggccgt agaccttgta tataccctgc accagcagtg accgggcaga gcccaacccc    1200
ctccacgggg gtcccagcac ccacttttct aatcatgaat gaacaataaa gcccacgctc    1260
tttgtcaggc tccacatgcc aaaaaaaaaa aaaaaaa                             1297

<210> SEQ ID NO 27
<211> LENGTH: 1132
<212> TYPE: DNA
<213> ORGANISM: Artificial Sequence
<220> FEATURE:
```

<223> OTHER INFORMATION: Mus musculus ninjurin 1 (Ninj1)

<400> SEQUENCE: 27

```
cccgggcggc cgcaccatgg agtcgggcac tgaggagtat gagctcaacg gcgacctgcg      60
cccgggctcc cccggttccc ccgacgcctt gccaccccgc tggggtttgc ggaaccggcc     120
catcaatgta aaccattatg ccaacaagaa gagcgctgcg gagagcatgc tggacatcgc     180
gctgctcatg gccaacgcgt cgcagctgaa ggccgtggtg gagcagggca atgatttcgc     240
cttcttcgtg cccccttgtgg tcctcatctc tatctccctc gtgctgcaga taggagtggg     300
cgtgctgctc atcttcctgg tcaagtatga cctcaacaac ccggccaagc acgccaagct     360
ggactttctt aacaacctgg ccacgggact ggttttcatc atcgtcgtgg tcaacatctt     420
cattacggcc ttcggggtcc agaagccgt aatggacgtg cgcccccggc agtagaacgc     480
ccagagactt aagggtacc ggacctgcag cccagctgac cagacccctg caactgctgt     540
acccccaagg tatccctctc ctgtgtgcag agcccaaggt ggccaccgct ggaccatggt     600
cagggacgga cttccgtcca actgtgaccg ctgtgtgggc ggccacctga acatgtgggg    660
aaccggatgc agggccatga agatcagaac tggacagctc catagaaacc caagtccaga    720
gaatggtcac tgcccaccca aggacatgca gcaaatccat gattgactt gacgaggggc    780
cagcactggc ctctgtctca ggacattcca gaaggaccag gatatgcccc tcccttgct    840
gatacaccag tgaccctact tctcatggag cctgcccagg tcaccctgga gactgctgcc    900
tttgttgttt cttgacccag ggaccttgga cagccatcag tatctgctgg ctccagcctc    960
agtgcctggg cttggcagcc atcaagaggc agccatgccc gtggggctg caggtcatgc   1020
tggtacttcc tgccagtggt gacctgggta gagccccagc cctcaactca ggggttcagg   1080
ccccactttt ctaatcagga acgacaataa agcttatgtg cttccctgct gg          1132
```

<210> SEQ ID NO 28
<211> LENGTH: 92
<212> TYPE: DNA
<213> ORGANISM: Artificial Sequence
<220> FEATURE:
<223> OTHER INFORMATION: IgG_VH-HC forward primer

<400> SEQUENCE: 28

```
attcgatcga tatggagaca gacacactcc tgctatgggt actgctgctc tgggttccag      60
gttccacgtg ggaggtgcag ctgttggagt ct                                    92
```

<210> SEQ ID NO 29
<211> LENGTH: 33
<212> TYPE: DNA
<213> ORGANISM: Artificial Sequence
<220> FEATURE:
<223> OTHER INFORMATION: IgG_VH-HC reverse primer

<400> SEQUENCE: 29

```
cttggtgcta gctgagctca cggtgaccag tgt                                   33
```

<210> SEQ ID NO 30
<211> LENGTH: 92
<212> TYPE: DNA
<213> ORGANISM: Artificial Sequence
<220> FEATURE:
<223> OTHER INFORMATION: IgG_VL-LC forward primer

<400> SEQUENCE: 30

```
attcgatcga tatggagaca gacacactcc tgctatgggt actgctgctc tgggttccag      60
```
gttccacgtg gcagtctgtg ctgactcagc ca                                    92

<210> SEQ ID NO 31
<211> LENGTH: 33
<212> TYPE: DNA
<213> ORGANISM: Artificial Sequence
<220> FEATURE:
<223> OTHER INFORMATION: IgG_VL-LC reverse primer

<400> SEQUENCE: 31
agccaccgta cgtaggaccg tcagcttggt gcc                                   33

<210> SEQ ID NO 32
<211> LENGTH: 28
<212> TYPE: DNA
<213> ORGANISM: Artificial sequence
<220> FEATURE:
<223> OTHER INFORMATION: synthetic sequence

<400> SEQUENCE: 32
tatggatccc tactgctggg gtgccatg                                         28

<210> SEQ ID NO 33
<211> LENGTH: 28
<212> TYPE: DNA
<213> ORGANISM: Artificial sequence
<220> FEATURE:
<223> OTHER INFORMATION: synthetic sequence

<400> SEQUENCE: 33
tatgaattca tggactcggg aaccgagg                                         28

<210> SEQ ID NO 34
<211> LENGTH: 19
<212> TYPE: PRT
<213> ORGANISM: Artificial Sequence
<220> FEATURE:
<223> OTHER INFORMATION: Cloning Vector

<400> SEQUENCE: 34

Leu Val Pro Arg Gly Ser Pro Glu Phe Pro Gly Arg Leu Glu Arg Pro
1               5                   10                  15

His Arg Asp

<210> SEQ ID NO 35
<211> LENGTH: 60
<212> TYPE: DNA
<213> ORGANISM: Artificial Sequence
<220> FEATURE:
<223> OTHER INFORMATION: Cloning Vector

<400> SEQUENCE: 35
ctggttccgc gtggatcccc ggaattcccg ggtcgactcg agcggccgca tcgtgactga     60

<210> SEQ ID NO 36
<211> LENGTH: 231
<212> TYPE: DNA
<213> ORGANISM: homo sapien

<400> SEQUENCE: 36
ggatccatgg actcgggaac cgaggagtac gagctcaacg gcggcctgcc tccgggcaca     60
cccggctccc cggacgcctc gccggcccgc tggggctgga ggcacgggcc catcaacgtg    120
aaccattacg ccagcaagaa gagcgcagcc gagagcatgc tggacatcgc gctgctgatg    180

```
gccaacgcgt cccagctgaa ggccgtcgtg aacagggct gataactcga g            231

<210> SEQ ID NO 37
<211> LENGTH: 231
<212> TYPE: DNA
<213> ORGANISM: mus musculus

<400> SEQUENCE: 37
ggatccatgg agtcgggcac tgaggagtat gagctcaacg gcgacctgcg cccgggctcc    60
cccggttccc ccgacgcctt gccaccccgc tggggtttgc ggaaccggcc catcaatgta   120
aaccattatg ccaacaagaa gagcgctgcg gagagcatgc tggacatcgc gctgctcatg   180
gccaacgcgt gccagctgaa ggccgtggtg gagcagggct gataactcga g            231
```